US012642755B2

(12) United States Patent
Boulemnakher et al.

(10) Patent No.: US 12,642,755 B2
(45) Date of Patent: Jun. 2, 2026

(54) COMPOSITION COMPRISING AT LEAST ONE OXIDATION DYE, 1,3-PROPANEDIOL, AT LEAST ONE ALKALINE AGENT AND AT LEAST ONE FATTY SUBSTANCE

(71) Applicant: L'Oreal, Paris (FR)

(72) Inventors: Sarah Boulemnakher, Saint-Ouen (FR); Maria Nieto, Saint-Ouen (FR); Julie Bruyere, Saint-Ouen (FR); Hanène Moueddene, Saint-Ouen (FR); Marie Giafferi, Saint-Ouen (FR); Laurence Cottard-Mei, Saint-Ouen (FR)

(73) Assignee: L'Oréal, Paris (FR)

( * ) Notice: Subject to any disclaimer, the term of this patent is extended or adjusted under 35 U.S.C. 154(b) by 0 days.

(21) Appl. No.: 18/574,814

(22) PCT Filed: Jun. 29, 2022

(86) PCT No.: PCT/EP2022/067983

§ 371 (c)(1),
(2) Date: Dec. 28, 2023

(87) PCT Pub. No.: WO2023/275193

PCT Pub. Date: Jan. 5, 2023

(65) Prior Publication Data

US 2024/0350387 A1 Oct. 24, 2024

(30) Foreign Application Priority Data

Jun. 30, 2021 (FR) ....................................... 2107050
Jun. 30, 2021 (FR) ....................................... 2107058

(51) Int. Cl.
*A61Q 5/10* (2006.01)
*A61K 8/34* (2006.01)
*A61K 8/41* (2006.01)
*A61K 8/49* (2006.01)

(52) U.S. Cl.
CPC .............. *A61K 8/415* (2013.01); *A61K 8/345* (2013.01); *A61K 8/4973* (2013.01); *A61Q 5/10* (2013.01); *A61K 2800/882* (2013.01)

(58) Field of Classification Search
CPC ...... A61K 8/415; A61K 8/345; A61K 8/4973; A61K 2800/882; A61K 8/411; A61K 8/41; A61K 8/4926; A61K 8/498; A61K 8/342; A61Q 5/10
USPC .............................................................. 8/405
See application file for complete search history.

(56) References Cited

U.S. PATENT DOCUMENTS

| | | | |
|---|---|---|---|
| 2,261,002 | A | 10/1941 | Ritter |
| 2,271,378 | A | 1/1942 | Searle |
| 2,273,780 | A | 2/1942 | Dittmar |
| 2,375,853 | A | 5/1945 | Kirby et al. |
| 2,388,614 | A | 11/1945 | Kirby et al. |
| 2,454,547 | A | 11/1948 | Bock et al. |
| 2,961,347 | A | 11/1960 | Floyd |
| 3,206,462 | A | 9/1965 | McCarty |
| 3,227,615 | A | 1/1966 | Korden |
| 3,472,840 | A | 10/1969 | Stone et al. |
| 3,589,978 | A | 6/1971 | Kamal et al. |
| 3,632,559 | A | 1/1972 | Matter et al. |
| 3,874,870 | A | 4/1975 | Green et al. |
| 3,910,862 | A | 10/1975 | Barabas et al. |
| 3,912,808 | A | 10/1975 | Sokol |
| 3,915,921 | A | 10/1975 | Schlatzer, Jr. |
| 3,917,817 | A | 11/1975 | Vanlerberghe et al. |
| 3,929,990 | A | 12/1975 | Green et al. |
| 3,966,904 | A | 6/1976 | Green et al. |
| 4,001,432 | A | 1/1977 | Green et al. |
| 4,003,699 | A | 1/1977 | Rose et al. |
| 4,005,193 | A | 1/1977 | Green et al. |
| 4,013,307 | A | 3/1977 | Dowd et al. |
| 4,025,617 | A | 5/1977 | Green et al. |
| 4,025,627 | A | 5/1977 | Green et al. |
| 4,025,653 | A | 5/1977 | Green et al. |
| 4,026,945 | A | 5/1977 | Green et al. |
| 4,027,020 | A | 5/1977 | Green et al. |
| 4,031,307 | A | 6/1977 | Demartino et al. |
| 4,075,136 | A | 2/1978 | Schaper |
| 4,131,576 | A | 12/1978 | Iovine et al. |
| 4,137,180 | A | 1/1979 | Naik et al. |
| 4,157,388 | A | 6/1979 | Christiansen |
| 4,165,367 | A | 8/1979 | Chakrabarti |
| 4,172,887 | A | 10/1979 | Vanlerberghe et al. |
| RE30,199 | E | 1/1980 | Rose et al. |
| 4,217,914 | A | 8/1980 | Jacquet et al. |
| 4,240,450 | A | 12/1980 | Grollier et al. |

(Continued)

FOREIGN PATENT DOCUMENTS

| | | | |
|---|---|---|---|
| CA | 2576189 | A1 | 6/2007 |
| CA | 2615230 | A1 | 4/2008 |

(Continued)

OTHER PUBLICATIONS

International Search Report in PCT/EP2022/067983, mailed Oct. 13, 2022, 3 pages.
International Preliminary Report on Patentability in PCT/EP2022/067983, mailed Dec. 14, 2023, 8 pages.
Katiuscia Grevalcuore et al., "Hair Care Compostion," Research Disclosure, Kenneth Mason Publications, Hampshire, UK, GB, vol. 671, No. 47, Mar. 1, 2020, pp. 286.
Porter, M.R., "Handbook of Surfactants," 1991, Blackie & Song, Glasgow and London, pp. 116-178.
Database Cosmetics—Coslng: XP055939854, "Substance: 2.3-Dihydro-2H-1,4-benzoxazin-6-ol," CAS No. 26021-57-8, Jan. 1, 2013, 1 page.

(Continued)

*Primary Examiner* — Eisa B Elhilo
(74) *Attorney, Agent, or Firm* — The Marbury Law Group, PLLC

(57) ABSTRACT

The invention relates to a composition comprising at least one oxidation dye, 1,3-propanediol, at least one alkaline agent and at least one fatty substance other than fatty acids.

20 Claims, No Drawings

(56) References Cited

U.S. PATENT DOCUMENTS

| | | | | |
|---|---|---|---|---|
| 4,333,730 | A | 6/1982 | Bugaut et al. | |
| 4,349,532 | A | 9/1982 | Vanlerberghe et al. | |
| 4,381,919 | A | 5/1983 | Jacquet et al. | |
| 4,509,949 | A | 4/1985 | Huang et al. | |
| 4,591,610 | A | 5/1986 | Grollier | |
| 4,702,906 | A | 10/1987 | Jacquet et al. | |
| 4,719,282 | A | 1/1988 | Nadolsky et al. | |
| 4,761,273 | A | 8/1988 | Grollier et al. | |
| 4,823,985 | A | 4/1989 | Grollier et al. | |
| 4,839,166 | A | 6/1989 | Grollier et al. | |
| 4,874,554 | A | 10/1989 | Lange et al. | |
| 4,904,275 | A | 2/1990 | Grollier | |
| 4,996,059 | A | 2/1991 | Grollier et al. | |
| 5,061,289 | A | 10/1991 | Clausen et al. | |
| 5,089,252 | A | 2/1992 | Grollier et al. | |
| 5,380,340 | A | 1/1995 | Neunhoeffer et al. | |
| 5,500,022 | A | 3/1996 | Cotteret | |
| 5,534,267 | A | 7/1996 | Neunhoeffer et al. | |
| 5,663,366 | A | 9/1997 | Neunhoeffer et al. | |
| 5,690,695 | A | 11/1997 | Cotteret et al. | |
| 5,766,576 | A | 6/1998 | Löwe et al. | |
| 5,769,901 | A | 6/1998 | Fishman | |
| 6,099,592 | A | 8/2000 | Vidal et al. | |
| 6,099,593 | A | 8/2000 | Terranova et al. | |
| 6,284,003 | B1 | 9/2001 | Rose et al. | |
| 6,287,578 | B1 | 9/2001 | Duetsch et al. | |
| 6,313,260 | B2 | 11/2001 | Gruning et al. | |
| 6,417,222 | B1 | 7/2002 | Vacher et al. | |
| 6,730,789 | B1 | 5/2004 | Birault et al. | |
| 8,444,713 | B2 | 5/2013 | Lim et al. | |
| 8,663,341 | B2 | 3/2014 | Sutton et al. | |
| 9,474,700 | B2 | 10/2016 | Salvemini et al. | |
| 10,226,649 | B2 | 3/2019 | Fujinuma et al. | |
| 10,555,891 | B2 | 2/2020 | Patterson et al. | |
| 11,213,471 | B2 | 1/2022 | Nicou et al. | |
| 12,290,586 | B2 | 5/2025 | Nicou | |
| 12,296,035 | B2 | 5/2025 | Paillard-Brunet et al. | |
| 12,390,408 | B2 | 8/2025 | Blanc et al. | |
| 12,533,306 | B2 | 1/2026 | Sabbagh et al. | |
| 12,569,402 | B2 | 3/2026 | Gong et al. | |
| 2002/0050013 | A1 | 5/2002 | Vidal et al. | |
| 2002/0119171 | A1 | 8/2002 | Gruning et al. | |
| 2003/0226217 | A1 | 12/2003 | Bowes et al. | |
| 2005/0188477 | A1 | 9/2005 | Plos | |
| 2007/0226917 | A1 | 10/2007 | Kleen et al. | |
| 2012/0210519 | A1 | 8/2012 | Lim et al. | |
| 2013/0081647 | A1 | 4/2013 | Vohra et al. | |
| 2013/0255004 | A1 | 10/2013 | Sutton et al. | |
| 2014/0053345 | A1 | 2/2014 | Rapold et al. | |
| 2014/0082855 | A1 | 3/2014 | Rapold et al. | |
| 2014/0353200 | A1 | 12/2014 | Samain et al. | |
| 2015/0182441 | A1* | 7/2015 | Goutsis | A61K 8/55 8/405 |
| 2015/0202125 | A1 | 7/2015 | Charrier et al. | |
| 2015/0335563 | A1 | 11/2015 | Allard et al. | |
| 2016/0158129 | A1 | 6/2016 | Neuba et al. | |
| 2016/0331673 | A1 | 11/2016 | Ferritto et al. | |
| 2017/0027832 | A1 | 2/2017 | Wang | |
| 2017/0258695 | A1 | 9/2017 | Consoli et al. | |
| 2017/0348210 | A1 | 12/2017 | Nicou et al. | |
| 2018/0326228 | A1 | 11/2018 | Nöcker et al. | |
| 2018/0338900 | A1 | 11/2018 | Patterson et al. | |
| 2019/0117541 | A1 | 4/2019 | Consoli et al. | |
| 2019/0224088 | A1 | 7/2019 | Gross et al. | |
| 2020/0093729 | A1 | 3/2020 | Mignon et al. | |
| 2020/0163851 | A1* | 5/2020 | Nicou | A61K 8/22 |
| 2020/0239206 | A1 | 7/2020 | Mckenzie et al. | |
| 2020/0261333 | A1 | 8/2020 | Grosjacques et al. | |
| 2020/0345604 | A1 | 11/2020 | Nicou et al. | |
| 2021/0177717 | A1 | 6/2021 | Consoli et al. | |
| 2024/0000682 | A1 | 1/2024 | Paillard-Brunet et al. | |
| 2024/0000683 | A1 | 1/2024 | Paillard-Brunet et al. | |
| 2024/0000685 | A1 | 1/2024 | Cottard-Mei | |
| 2024/0050343 | A1 | 2/2024 | Sabbagh et al. | |
| 2024/0058247 | A1 | 2/2024 | Cottard-Mei et al. | |
| 2024/0065955 | A1 | 2/2024 | Nicou et al. | |
| 2024/0074960 | A1 | 3/2024 | Nicou et al. | |
| 2024/0115472 | A1 | 4/2024 | Nicou et al. | |
| 2024/0285494 | A1 | 8/2024 | Boulemnakher et al. | |
| 2024/0285498 | A1 | 8/2024 | Boulemnakher et al. | |
| 2024/0335363 | A1 | 10/2024 | Moueddene et al. | |
| 2025/0009624 | A1 | 1/2025 | Sabbagh et al. | |
| 2025/0025398 | A1 | 1/2025 | Sabbagh et al. | |
| 2025/0032386 | A1 | 1/2025 | Blanc et al. | |
| 2025/0041182 | A1 | 2/2025 | Nicou et al. | |
| 2025/0041187 | A1 | 2/2025 | Blanc et al. | |
| 2025/0049669 | A1 | 2/2025 | Sabbagh et al. | |
| 2025/0049670 | A1 | 2/2025 | Nicou et al. | |
| 2025/0049671 | A1 | 2/2025 | Blanc et al. | |
| 2025/0049694 | A1 | 2/2025 | Blanc et al. | |

FOREIGN PATENT DOCUMENTS

| | | | |
|---|---|---|---|
| DE | 2359399 | A1 | 6/1975 |
| DE | 3843892 | A1 | 6/1990 |
| DE | 4133957 | A1 | 4/1993 |
| DE | 19543988 | A1 | 5/1997 |
| DE | 202009011154 | U1 | 10/2009 |
| EP | 0080976 | A1 | 6/1983 |
| EP | 0122324 | A1 | 10/1984 |
| EP | 0173109 | A2 | 3/1986 |
| EP | 0216479 | A1 | 4/1987 |
| EP | 0317542 | A2 | 5/1989 |
| EP | 0337354 | A1 | 10/1989 |
| EP | 0399133 | A1 | 11/1990 |
| EP | 0459901 | A1 | 12/1991 |
| EP | 0509382 | A2 | 10/1992 |
| EP | 0516102 | A1 | 12/1992 |
| EP | 0684035 | A1 | 11/1995 |
| EP | 0767191 | A2 | 4/1997 |
| EP | 0770375 | A1 | 5/1997 |
| EP | 0884344 | A2 | 12/1998 |
| EP | 0959090 | A1 | 11/1999 |
| EP | 0959091 | A1 | 11/1999 |
| EP | 0959094 | A1 | 11/1999 |
| EP | 1428510 | A1 | 6/2004 |
| EP | 1518544 | A1 | 3/2005 |
| EP | 1559409 | A1 | 8/2005 |
| EP | 2926802 | A1 | 10/2015 |
| EP | 3181115 | A1 | 6/2017 |
| EP | 3287120 | A1 | 2/2018 |
| EP | 3295923 | A1 | 3/2018 |
| EP | 3295924 | A1 | 3/2018 |
| EP | 3777822 | A1 | 2/2021 |
| FR | 1492597 | A | 8/1967 |
| FR | 1583363 | A | 10/1969 |
| FR | 2077143 | A5 | 10/1971 |
| FR | 2080759 | A1 | 11/1971 |
| FR | 2162025 | A1 | 7/1973 |
| FR | 2190406 | A2 | 2/1974 |
| FR | 2252840 | A1 | 6/1975 |
| FR | 2270846 | A1 | 12/1975 |
| FR | 2280361 | A2 | 2/1976 |
| FR | 2316271 | A1 | 1/1977 |
| FR | 2320330 | A1 | 3/1977 |
| FR | 2336434 | A1 | 7/1977 |
| FR | 2368508 | A2 | 5/1978 |
| FR | 2393573 | A1 | 1/1979 |
| FR | 2413907 | A1 | 8/1979 |
| FR | 2470596 | A1 | 6/1981 |
| FR | 2505348 | A1 | 11/1982 |
| FR | 2519863 | A1 | 7/1983 |
| FR | 2542997 | A1 | 9/1984 |
| FR | 2575067 | A1 | 6/1986 |
| FR | 2586913 | A1 | 3/1987 |
| FR | 2598611 | A1 | 11/1987 |
| FR | 2733749 | A1 | 11/1996 |
| FR | 2750048 | A1 | 12/1997 |
| FR | 2801308 | A1 | 5/2001 |
| FR | 2886136 | A1 | 12/2006 |
| FR | 2984148 | A1 | 6/2013 |
| FR | 2988591 | A1 | 10/2013 |
| FR | 2988594 | A1 | 10/2013 |
| FR | 2988595 | A1 | 10/2013 |

(56) References Cited

FOREIGN PATENT DOCUMENTS

| | | | |
|---|---|---|---|
| FR | 2988598 | A1 | 10/2013 |
| FR | 3026005 | A1 | 3/2016 |
| FR | 3026007 | A1 | 3/2016 |
| FR | 30260006 | A1 | 3/2016 |
| FR | 3045345 | A1 | 6/2017 |
| FR | 3045379 | A1 | 6/2017 |
| FR | 3046071 | A1 | 6/2017 |
| GB | 1026978 | A | 4/1966 |
| GB | 1153196 | A | 5/1969 |
| GB | 1546809 | A | 5/1979 |
| GB | 2521426 | A | 6/2015 |
| IT | 201900005622 | A1 | 10/2020 |
| JP | H0219576 | A | 1/1990 |
| JP | H05163124 | A | 6/1993 |
| JP | H08169571 | A | 7/1996 |
| JP | 2017160198 | A | 9/2017 |
| KR | 1020170015063 | A | 2/2017 |
| WO | 9408969 | A1 | 4/1994 |
| WO | 9408970 | A1 | 4/1994 |
| WO | 9615765 | | 5/1996 |
| WO | 9844012 | A1 | 10/1998 |
| WO | 0058282 | A2 | 10/2000 |
| WO | 2004024779 | A2 | 3/2004 |
| WO | 2005102253 | A1 | 11/2005 |
| WO | 2009060334 | A2 | 5/2009 |
| WO | 2010139878 | A2 | 12/2010 |
| WO | 2011034868 | A1 | 3/2011 |
| WO | 2013144260 | A2 | 10/2013 |
| WO | 2016/097229 | A1 | 6/2016 |
| WO | 2016096654 | A1 | 6/2016 |
| WO | 2016097228 | A1 | 6/2016 |
| WO | 2016177344 | A1 | 11/2016 |
| WO | 2016177345 | A1 | 11/2016 |
| WO | 2017108841 | A1 | 6/2017 |
| WO | 2018053177 | A1 | 3/2018 |
| WO | 2018058209 | A1 | 4/2018 |
| WO | 2018/114886 | A1 | 6/2018 |
| WO | 2022129349 | A1 | 6/2022 |
| WO | 2022129357 | A1 | 6/2022 |
| WO | 2022129379 | A1 | 6/2022 |
| WO | 2022129385 | A1 | 6/2022 |
| WO | 2022129386 | A1 | 6/2022 |
| WO | 2022129388 | A1 | 6/2022 |
| WO | 2022129389 | A1 | 6/2022 |
| WO | 2022129393 | A1 | 6/2022 |
| WO | 2022129394 | A1 | 6/2022 |
| WO | 2023072944 | A1 | 5/2023 |
| WO | 2023073128 | A1 | 5/2023 |
| WO | 2023073130 | A1 | 5/2023 |
| WO | 2023073131 | A3 | 5/2023 |
| WO | 2023073133 | A1 | 5/2023 |
| WO | 2023073135 | A1 | 5/2023 |
| WO | 2023073136 | A1 | 5/2023 |
| WO | 2023105015 | A1 | 6/2023 |
| WO | 2023105016 | A1 | 6/2023 |
| WO | 2023105019 | A1 | 6/2023 |
| WO | 2023105021 | A1 | 6/2023 |
| WO | 2023105022 | A1 | 6/2023 |
| WO | 2023105025 | A1 | 6/2023 |

OTHER PUBLICATIONS

Database Cosmetics—Coslng: XP055939863, "Substance: Hydroxyethyl-3,4 methylenedioxyaniline and its hydrochloride," CAS No. 94158-14-2, Jan. 1, 2013, 1 page.
Database GNPD Mintel: XP055921611, "Permanent Hair Colour," Coty, Accession No. 5494631, Mar. 2, 2018.
Database GNPD Mintel: XP055921616, "Conditioning Colour," Coty, Accession No. 7425281, Mar. 6, 2020.
Database GNPD Mintel: XP055921775, "Discreet Grey Toning," Coty, Accession No. 8768207, Jun. 7, 2021.
Fonnum et al. "Associative thickeners. Part I: Synthesis, rheology and aggregation behavior." Colloid and Polymer Science 271.4 (1993): 380-389.
International Preliminary Report on Patentability in PCT/EP2022/079806, mailed May 10, 2024, 6 pages.
International Preliminary Report on Patentability in PCT/EP2022/085104, mailed Jun. 20, 2024, 7 pages.
International Preliminary Report on Patentability in PCT/EP2022/085109, mailed Jun. 20, 2024, 7 pages.
International Search Report and Written Opinion in PCT/EP2021/086275, dated Mar. 30, 2022, 9 pages.
International Search Report and Written Opinion in PCT/EP2021/086278, dated Apr. 11, 2022, 12 pages.
International Search Report and Written Opinion in PCT/EP2021/086279, dated Mar. 24, 2022, 12 pages.
International Search Report and Written Opinion in PCT/EP2021/086285, dated May 13, 2022, 12 pages.
International Search Report and Written Opinion in PCT/EP2021/086287, dated May 18, 2022, 12 pages.
International Search Report and Written Opinion in PCT/EP2021/976266, dated Apr. 11, 2022, 17 pages.
International Search Report and Written Opinion in PCT/EP2022/079806, mailed Feb. 20, 2023, 8 pages.
International Search Report and Written Opinion in PCT/EP2022/080128, dated Apr. 5, 2023, 8 pages.
International Search Report and Written Opinion in PCT/EP2022/080130, dated Mar. 13, 2023, 7 pages.
International Search Report and Written Opinion in PCT/EP2022/080132, dated May 2, 2023, 7 pages.
International Search Report and Written Opinion in PCT/EP2022/080134, dated Apr. 14, 2023, 7 pages.
International Search Report and Written Opinion in PCT/EP2022/080137, dated Mar. 17, 2023, 11 pages.
International Search Report and Written Opinion in PCT/EP2022/080139, dated Apr. 13, 2023, 7 pages.
International Search Report and Written Opinion in PCT/EP2022/085098, dated Mar. 2, 2023, 10 pages.
International Search Report and Written Opinion in PCT/EP2022/085100, dated Mar. 3, 2023, 11 pages.
International Search Report and Written Opinion in PCT/EP2022/085104, mailed Mar. 9, 2023, 10 pages.
International Search Report and Written Opinion in PCT/EP2022/085106, dated Mar. 6, 2023, 8 pages.
International Search Report and Written Opinion in PCT/EP2022/085109, mailed Mar. 9, 2023, 10 pages.
International Search Report and Written Opinion in PCT/EP2022/085113, dated Mar. 9, 2023, 10 pages.
International Search Report in PCT/EP2021/086274, dated Apr. 8, 2022, 4 pages.
Noll, W. "Chemistry and Technology of Silicones." Academis Press, New York, San Francisco, London (1968): 1-23.
Non-Final Office Action in U.S. Appl. No. 18/037,247, mailed Aug. 16, 2024, 7 pages.
Non-Final Office Action in U.S. Appl. No. 18/253,667, mailed Aug. 20, 2025, 45 pages.
Non-Final Office Action in U.S. Appl. No. 18/253,820, mailed Aug. 19, 2024, 9 pages.
Final Office Action in U.S. Appl. No. 18/253,820, mailed Nov. 27, 2024, 6 pages.
Non-Final Office Action in U.S. Appl. No. 18/253,820, mailed Jun. 4, 2025, 7 pages.
Non-Final Office Action in U.S. Appl. No. 18/266,726, mailed Aug. 27, 2024, 8 pages.
Final Office Action in U.S. Appl. No. 18/266,726, mailed Dec. 12, 2024, 7 pages.
Non-Final Office Action in U.S. Appl. No. 18/266,729, mailed Aug. 29, 2024, 10 pages.
Final Office Action in U.S. Appl. No. 18/266,729, mailed Dec. 12, 2024, 6 pages.
Non-Final Office Action in U.S. Appl. No. 18/266,729, mailed Apr. 29, 2025, 9 pages.
Non-Final Office Action in U.S. Appl. No. 18/268,088, mailed Mar. 31, 2025, 7 pages.
Non-Final Office Action in U.S. Appl. No. 18/704,694, mailed Apr. 2, 2025, 8 pages.

(56) References Cited

OTHER PUBLICATIONS

Non-Final Office Action in U.S. Appl. No. 18/704,698, mailed Apr. 18, 2025, 7 pages.
Final Office Action in U.S. Appl. No. 18/717,318, mailed Oct. 22, 2025, 5 pages.
Non-Final Office Action in U.S. Appl. No. 18/717,326, mailed May 27, 2025, 8 pages.
Restriction Requirement in U.S. Appl. No. 18/037,294, mailed Jul. 11, 2025, 10 pages.
Restriction Requirement in U.S. Appl. No. 18/253,667, mailed Jun. 25, 2025, 11 pages.
STIC Search Report in U.S. Appl. No. 18/037,247, dated Jul. 25, 2024, 83 pages.
Todd et al. "Volatile silicone fluids for cosmetic formulations." Cosmetics and Toiletries, vol. 91 (1976): 29-32.
U.S. Appl. No. 18/717,318, filed Jun. 6, 2024, 62 pages.
U.S. Appl. No. 18/717,326, filed Jun. 6, 2024, 56 pages.
Final Office Action for U.S. Appl. No. 18/268,088, mailed Dec. 23, 2025, 6 pages.
Non-Final Office Action for copending U.S. Appl. No. 18/037,294, dated Oct. 23, 2025.
Goh, C., New cationic conditioning polymers for hair care, 2006, Cosmetics Business, [retrieved Oct. 15, 2025], https://cosmeticsbusiness.com/new-cationic-conditioning-polymers-for-hair-care-47152) (Year: 2006).
Non-Final Office Action for copending U.S. Appl. No. 18/717,311, dated May 22, 2025.
Notice of Allowance for copending U.S. Appl. No. 18/253,820, dated Nov. 5, 2025.
International Search Report and Written Opinion for counterpart Application No. PCT/EP2021/086270, dated Apr. 11, 2022.
Mintel: "Permanent Hair Colour," Tints of Nature, Record ID 8023403, XP55849542, Aug. 13, 2020.
Mintel: "Root Retouch Crème," Laboratorios Phergal, Record ID 6480799, XP55849534, dated Apr. 16, 2019.
Non-Final Office Action for copending U.S. Appl. No. 18/267,927, dated Sep. 20, 2024.
Final Office Action for copending U.S. Appl. No. 18/267,927, dated Feb. 10, 2025.
Non-Final Office Action for copending U.S. Appl. No. 18/267,927, dated May 23, 2025.
Final Office Action for copending U.S. Appl. No. 18/268,088, dated Dec. 23, 2025.
Final Office Action for copending U.S. Appl. No. 18/717,318, dated Oct. 22, 2025.
Non-Final Office Action for copending U.S. Appl. No. 18/717,308, dated May 22, 2025.
Grevalcuore et al., "Hair Care Composition," Research Disclosure, Kenneth Mason Publications, Hampshire, UK, GB, vol. 672, No. 75, Apr. 1, 2020.
Non-Final Office Action in U.S. Appl. No. 18/704,686, mailed Apr. 8, 2026, 64 pages.
Final Office Action in U.S. Appl. No. 18/253,667, mailed Apr. 23, 2026, 79 pages.
Restriction Requirement in U.S. Appl. No. 18/704,690, mailed Mar. 26, 2026, 9 pages.

* cited by examiner

COMPOSITION COMPRISING AT LEAST ONE OXIDATION DYE, 1,3-PROPANEDIOL, AT LEAST ONE ALKALINE AGENT AND AT LEAST ONE FATTY SUBSTANCE

CROSS REFERENCE TO RELATED APPLICATIONS

This is a National Stage Application of PCT/EP2022/067983, filed internationally on Jun. 29, 2022, which claims priority to French Application Nos. 2107050 and 2017058, both filed on Jun. 30, 2021, the contents of all of which are incorporated by reference herein in their entireties.

The invention relates to a composition comprising at least one oxidation dye, 1,3-propanediol, at least one alkaline agent and at least one fatty substance other than fatty acids.

The invention also relates to a process for dyeing keratin fibres, notably the hair, using this composition.

Finally, the invention relates to the use of such a composition for dyeing keratin fibres, and notably the hair.

Many people have sought for a long time to modify the colour of their hair and in particular to mask their grey hair.

It is known practice to dye keratin fibres, in particular human keratin fibres such as the hair, to obtain "permanent" colourings with dyeing compositions containing oxidation dye precursors, notably oxidation bases, such as ortho- or para-phenylenediamines, ortho- or para-aminophenols, or heterocyclic compounds such as pyrazoles, pyrazolinones or pyrazolo-pyridines. These oxidation bases are colourless or weakly coloured compounds which, when combined with oxidizing products, may give rise to coloured compounds via a process of oxidative condensation.

It is also possible to vary the shades obtained with these oxidation bases by combining them with couplers or colour modifiers. The variety of molecules used as oxidation bases and couplers allows a wide range of colours to be obtained.

However, the use of these dye compositions may have a certain number of drawbacks.

Specifically, after application to keratin fibres, the dyeing power obtained may not be entirely satisfactory, or may even be weak, and lead to a restricted range of colours.

The colourings may also be insufficiently persistent with respect to external agents such as light, shampoo or perspiration, and may also be too selective, i.e. the difference in colouring is too great along the same keratin fibre that is differently sensitized between its end and its root.

Moreover, the regulatory conditions regarding certain compounds are increasingly stringent. It is thus necessary to develop compositions comprising alternative compounds.

Consumers are moreover in search of dyeing products that are more environmentally friendly, notably based on ingredients of natural origin, and which have good working qualities, are easy to use and give good dyeing properties.

Thus, there is a real need for a composition for dyeing keratin fibres, in particular human keratin fibres such as the hair, which is more environmentally friendly and which does not have the abovementioned drawbacks, i.e. which is capable of giving good colour build-up, intensity and chromaticity while at the same time having low selectivity and good persistence and which is capable of giving good dyeing performance, even after a period of storage, while at the same time having good working qualities.

These aims and others are achieved by the present invention, one subject of which is thus a composition comprising:

one or more oxidation dyes chosen from at least one coupler chosen from: 6-hydroxybenzomorpholine of formula (I), the addition salts thereof, the solvates thereof and/or the solvates of the salts thereof, hydroxyethyl-3,4-methylenedioxyaniline of formula (II), the addition salts thereof, the solvates thereof and/or the solvates of the salts thereof, 2-amino-5-ethylphenol of formula (III), the addition salts thereof, the solvates thereof and/or the solvates of the salts thereof, and mixtures thereof;

(I)

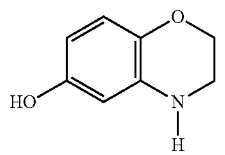

(II)

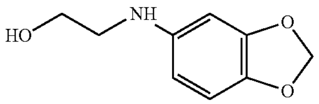

(III)

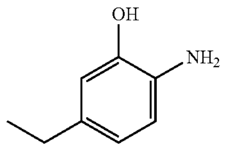

at least one base chosen from: 2-p-hydroxyethyl-para-phenylenediamine and the addition salts thereof, the solvates thereof and/or the solvates of salts thereof, 2-(γ-hydroxy-propyl)-para-phenylenediamine and the addition salts thereof, the solvates thereof and/or the solvates of salts thereof, 2-methoxymethyl-para-phenylenediamine and the addition salts thereof, the solvates thereof and/or the solvates of salts thereof, and mixtures thereof;

1,3-propanediol;

at least one alkaline agent;

at least one fatty substance other than fatty acids.

Preferably, the composition according to the invention comprises:

at least one coupler chosen from: 6-hydroxybenzomorpholine of formula (I), the addition salts thereof, the solvates thereof and/or the solvates of the salts thereof, hydroxyethyl-3,4-methylenedioxyaniline of formula (II), the addition salts thereof, the solvates thereof and/or the solvates of the salts thereof, 2-amino-5-ethylphenol of formula (III), the addition salts thereof, the solvates thereof and/or the solvates of the salts thereof, and mixtures thereof;

(I)

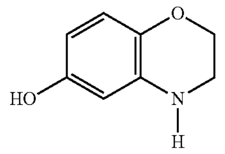

(II)

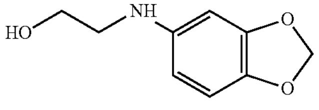

-continued (III)

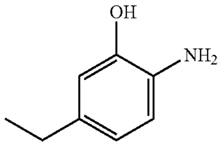

1,3-propanediol;

at least one alkaline agent;

at least one fatty substance other than fatty acids.

According to one variant, the composition according to the invention comprises:

at least one base chosen from: 2-p-hydroxyethyl-para-phenylenediamine and the addition salts thereof, the solvates thereof and/or the solvates of salts thereof, 2-(γ-hydroxypropyl)-para-phenylenediamine and the addition salts thereof, the solvates thereof and/or the solvates of salts thereof, 2-methoxymethyl-para-phenylenediamine and the addition salts thereof, the solvates thereof and/or the solvates of salts thereof, and mixtures thereof;

1,3-propanediol;

at least one alkaline agent;

at least one fatty substance other than fatty acids.

According to this variant, preferably, the composition according to the invention comprises:

at least one base chosen from: 2-p-hydroxyethyl-para-phenylenediamine and the addition salts thereof, the solvates thereof and/or the solvates of salts thereof, 2-(γ-hydroxypropyl)-para-phenylenediamine and the addition salts thereof, the solvates thereof and/or the solvates of salts thereof, 2-methoxymethyl-para-phenylenediamine and the addition salts thereof, the solvates thereof and/or the solvates of salts thereof, and mixtures thereof;

1,3-propanediol;

at least one alkaline agent;

at least one fatty substance other than fatty acids and at least one oxidation coupler.

In this variant, the oxidation coupler(s) may be chosen from all the oxidation couplers as defined hereinbelow.

According to a preferred embodiment, the composition according to the invention is a composition for dyeing keratin fibres, notably the hair.

The composition according to the invention may notably lead to chromatic, powerful, intense and sparingly selective colourings, i.e. colourings that are uniform along the length of the fibre. It also allows various shades to be achieved in a very wide range of colours. It also enables good colour build-up.

This composition also gives particularly good coverage of depigmented keratin fibres such as grey hair.

Moreover, the composition according to the invention has good working qualities, notably a creamy texture allowing quick and easy mixing with an oxidizing composition, where appropriate, and easy and uniform spreading over the entire head of hair. The composition according to the invention has good stability over time, notably little or no change in its viscosity during storage.

A subject of the invention is also a kit comprising, in a first compartment, a composition as defined previously and, in a second compartment, an oxidizing composition comprising at least one chemical oxidizing agent.

According to the invention, the term "chemical oxidizing agent" means an oxidizing agent other than atmospheric oxygen.

Other subjects, features, aspects and advantages of the invention will emerge even more clearly on reading the description and the examples that follow.

In the text hereinbelow, unless otherwise indicated, the limits of a range of values are included in that range, notably in the expressions "between" and "ranging from . . . to . . . ".

Moreover, the expression "at least one" used in the present description is equivalent to the expression "one or more".

The term "oxidation dyes" means dyes chosen from oxidation couplers and oxidation bases.

Couplers

The composition according to the invention may comprise one or more oxidation couplers. According to one variant, the composition according to the invention comprises at least one particular coupler.

The composition according to the present invention comprises one or more couplers chosen from: 6-hydroxybenzomorpholine of formula (I), the addition salts thereof, the solvates thereof and/or the solvates of the salts thereof, hydroxyethyl-3,4-methylenedioxyaniline of formula (II), the addition salts thereof, the solvates thereof and/or the solvates of the salts thereof, 2-amino-5-ethylphenol of formula (III), the addition salts thereof, the solvates thereof and/or the solvates of the salts thereof, and mixtures thereof.

The addition salts of the compounds of formulae (I), (II) and (III) are notably chosen from the addition salts with an acid, such as the hydrochlorides, hydrobromides, sulfates, citrates, succinates, tartrates, lactates, tosylates, benzenesulfonates, phosphates and acetates, and the addition salts with a base such as sodium hydroxide, potassium hydroxide, aqueous ammonia, amines or alkanolamines.

Moreover, the solvates of the compounds of formulae (I), (II) and (III) more particularly represent the hydrates of these compounds and/or the combination of these compounds with a linear or branched C1 to C4 alcohol such as methanol, ethanol, isopropanol or n-propanol. Preferably, the solvates are hydrates.

The total content of the couplers chosen from the compounds of formulae (I), (II) and (III) and also the addition salts thereof, the solvates thereof and/or the solvates of the salts thereof preferably ranges from 0.001% to 20% by weight, more preferentially from 0.005% to 15% by weight, better still from 0.01% to 10% by weight, even better still from 0.05% to 5% by weight, and even better still from 0.1% to 3% by weight, relative to the total weight of the composition.

When they are present, the total content of the couplers chosen from 6-hydroxybenzomorpholine of formula (I), the addition salts thereof, the solvates thereof and/or the solvates of the salts thereof preferably ranges from 0.001% to 20% by weight, more preferentially from 0.005% to 15% by weight, better still 0.01% to 10% by weight, even better still from 0.05% to 5% by weight, and even better still from 0.1% to 3% by weight, relative to the total weight of the composition.

When they are present, the total content of the couplers chosen from hydroxyethyl-3,4-methylenedioxyaniline of formula (II), the addition salts thereof, the solvates thereof and/or the solvates of the salts thereof preferably ranges from 0.001% to 20% by weight, more preferentially from 0.005% to 15% by weight, better still from 0.01% to 10% by weight, even better still from 0.05% to 5% by weight, and even better still from 0.1% to 3% by weight, relative to the total weight of the composition.

When they are present, the total content of the couplers chosen from 2-amino-5-ethylphenol of formula (III), the addition salts thereof, the solvates thereof and/or the solvates of the salts thereof preferably ranges from 0.001% to 20% by weight, more preferentially from 0.005% to 15% by weight, better still from 0.01% to 10% by weight, even better still from 0.05% to 5% by weight, and even better still from 0.1% to 3% by weight, relative to the total weight of the composition.

The composition according to the invention may optionally also comprise one or more additional couplers, other than the compounds of formulae (I), (II) and (III) and the addition salts thereof, the solvates thereof and/or the solvates of the salts thereof advantageously chosen from those conventionally used in the dyeing of keratin fibres.

Among the additional couplers, mention may be made in particular of meta-phenylenediamines, meta-aminophenols, meta-diphenols, naphthalene-based coupling agents and heterocyclic coupling agents, and also the corresponding addition salts, the solvates and solvates of the salts thereof.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, α-naphthol, 2-methyl-1-naphthol, 6-hydroxyindole, 4-hydroxyindole, 4-hydroxy-N-methylindole, 2-amino-3-hydroxypyridine, 3,5-diamino-2,6-dimethoxypyridine, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b][1,2,4]triazole, 2,6-dimethyl[3,2-c][1,2,4]triazole and 6-methylpyrazolo[1,5-a]benzimidazole, 2-methyl-5-aminophenol, 5-N-(β-hydroxyethyl)amino-2-methylphenol, 3-aminophenol and 3-amino-2-chloro-6-methylphenol, the corresponding addition salts, the solvates and solvates of the salts thereof, and the corresponding mixtures.

In general, the addition salts of the couplers that may be used in the context of the invention are chosen in particular from addition salts with an acid, such as hydrochlorides, hydrobromides, sulfates, citrates, succinates, tartrates, lactates, tosylates, benzenesulfonates, phosphates and acetates, and the addition salts with a base such as sodium hydroxide, potassium hydroxide, aqueous ammonia, amines or alkanolamines. Moreover, the solvates more particularly represent the hydrates of these couplers and/or the combination of these couplers with a linear or branched C1 to C4 alcohol such as methanol, ethanol, isopropanol or n-propanol. Preferably, the solvates are hydrates.

In a particular embodiment, the composition according to the invention is free of oxidation couplers chosen from resorcinol, 2-methylresorcinol, 4-chlororesorcinol, the addition salts thereof, the solvates thereof and the solvates of the salts thereof.

When the composition comprises one or more additional oxidation couplers, the total content of the additional coupler(s), other than the couplers of formulae (I), (II) and (III), salts thereof, solvates thereof and solvates of the salts thereof, present in the composition according to the invention, ranges from 0.001% to 20% by weight, more preferentially from 0.005% to 15% by weight, better still from 0.01% to 10% by weight, even better still from 0.05% to 5% by weight, and even better still from 0.1% to 3% by weight, relative to the total weight of the composition.

1,3-Propanediol

The composition according to the invention comprises 1,3-propanediol.

Preferably, the total content of 1,3-propanediol ranges from 0.01% to 25% by weight, more preferentially from 0.1% to 20% by weight, better still from 1% to 15% by weight, even better still from 2% to 10% by weight, and even better still from 3% to 8% by weight, relative to the total weight of the composition.

Alkaline Agent

The composition according to the present invention comprises one or more mineral, organic or hybrid alkaline agents.

For the purposes of the present invention, the terms “alkaline agent” and “basifying agent” are used interchangeably.

The mineral basifying agent(s) are preferably chosen from aqueous ammonia, alkali metal carbonates or bicarbonates such as sodium (hydrogen) carbonate and potassium (hydrogen) carbonate, alkali metal or alkaline-earth metal phosphates such as sodium phosphates or potassium phosphates, sodium or potassium hydroxides, and mixtures thereof.

The organic basifying agent(s) are preferably chosen from alkanolamines, amino acids, organic amines other than alkanolamines, oxyethylenated and/or oxypropylenated ethylenediamines, 1,3-diaminopropane, spermine, spermidine and mixtures thereof.

The term “alkanolamine” means an organic amine comprising a primary, secondary or tertiary amine function, and one or more linear or branched $C_1$-$C_8$ alkyl groups bearing one or more hydroxyl radicals.

Organic amines chosen from alkanolamines such as monoalkanolamines, dialkanolamines or trialkanolamines comprising one to three identical or different $C_1$-$C_4$ hydroxyalkyl radicals are in particular suitable for performing the invention.

In particular, the alkanolamine(s) are chosen from monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethyl)aminomethane and mixtures thereof.

Advantageously, the amino acids are basic amino acids comprising an additional amine function. Such basic amino acids are preferably chosen from histidine, lysine, arginine, ornithine and citrulline.

The organic amine may also be chosen from organic amines of heterocyclic type. Besides histidine that has already been mentioned in the amino acids, mention may in particular be made of pyridine, piperidine, imidazole, triazole, tetrazole and benzimidazole. The organic amine may also be chosen from amino acid dipeptides. As amino acid dipeptides that may be used in the present invention, mention may notably be made of carnosine, anserine and balenine. The organic amine may also be chosen from compounds including a guanidine function. As amines of this type other than arginine that may be used in the present invention, mention may notably be made of creatine, creatinine, 1,1-dimethylguanidine, 1,1-diethylguanidine, glycocyamine, metformin, agmatine, n-amidoalanine, 3-guanidinopropionic acid, 4-guanidinobutyric acid and 2-([amino(imino)methyl]amino)ethane-1-sulfonic acid.

Guanidine carbonate or monoethanolamine hydrochloride may in particular be used as hybrid compounds.

The alkaline agent(s) that are useful according to the invention are preferably chosen from alkanolamines such as monoethanolamine, diethanolamine, triethanolamine; aqueous ammonia, carbonates or bicarbonates such as sodium (hydrogen) carbonate and potassium (hydrogen) carbonate, alkali metal or alkaline-earth metal silicates or metasilicates such as sodium metasilicate, and mixtures thereof, more preferentially from alkanolamines and aqueous ammonia, better still from alkanolamines, and even better still monoethanolamine.

In a particular embodiment, the composition according to the invention is free of aqueous ammonia.

The total content of the alkaline agent(s) preferably ranges from 0.1% to 40% by weight, more preferentially from 1% to 30% by weight, better still from 2% to 25% by weight, and even better still from 4% to 20% by weight, relative to the total weight of the composition.

According to one particular embodiment, the total content of alkanolamine, preferably of monoethanolamine, preferably ranges from 0.1% to 40% by weight, more preferentially from 1% to 30% by weight, better still from 2% to 25% by weight, and even better still from 4% to 20% by weight, or even from 8% to 15% by weight, relative to the total weight of the composition.

According to one particular embodiment, the composition according to the invention comprises at least one (meta) silicate. According to this embodiment, the total content of alkali metal or alkaline-earth metal silicates or metasilicates, preferably of sodium metasilicate, preferably ranges from 0.01% to 20% by weight, more preferentially from 0.1% to 10% by weight, better still from 0.2% to 5% by weight, and even better still from 0.5% to 2% by weight, relative to the total weight of the composition.

According to one embodiment, the pH of the composition according to the invention is between 8 and 13; preferably between 9.0 and 12.

The pH of the composition may be adjusted to the desired value by means of acidic or alkaline agent(s) commonly used in the dyeing of keratin fibres, such as those described previously, or alternatively using buffer systems known to those skilled in the art.

Fatty Substances Other than Fatty Acids

The composition according to the invention comprises one or more fatty substances other than fatty acids.

By other than fatty acids is meant other than free fatty acids.

The term "fatty substance" means an organic compound that is insoluble in water at 25° C. and at atmospheric pressure ($1.013\times10^5$ Pa) (solubility of less than 5% by weight, preferably less than 1% by weight, even more preferentially less than 0.1% by weight). They bear in their structure at least one hydrocarbon-based chain including at least 6 carbon atoms and/or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

The fatty substances that may be used in the present invention are neither (poly)oxyalkylenated nor (poly)glycerolated.

Preferably, the fatty substances that are useful according to the invention are non-silicone.

The term "non-silicone fatty substance" refers to a fatty substance not containing any Si—O bonds and the term "silicone fatty substance" refers to a fatty substance containing at least one Si—O bond.

The fatty substances that are useful according to the invention can be liquid fatty substances (or oils) and/or solid fatty substances. The term "liquid fatty substance" means a fatty substance with a melting point of less than or equal to 25° C. at atmospheric pressure ($1.013\times10^5$ Pa) and the term "solid fatty substance" means a fatty substance with a melting point of greater than 25° C. at atmospheric pressure ($1.013\times10^5$ Pa).

For the purposes of the present invention, the melting point corresponds to the temperature of the most endothermic peak observed on thermal analysis (differential scanning calorimetry or DSC) as described in the standard ISO 11357-3; 1999. The melting point may be measured using a differential scanning calorimeter (DSC), for example the calorimeter sold under the name MDSC 2920 by the company TA Instruments. In the present patent application, all the melting points are determined at atmospheric pressure ($1.013\times10^5$ Pa).

More particularly, the liquid fatty substance(s) may be chosen from C6 to C16 liquid hydrocarbons, liquid hydrocarbons comprising more than 16 carbon atoms, non-silicone oils of animal origin, oils of triglyceride type of plant or synthetic origin, fluoro oils, liquid fatty alcohols, liquid esters of fatty acid and/or of fatty alcohol other than triglycerides, and mixtures thereof.

It is recalled that the fatty alcohols and esters more particularly contain at least one saturated or unsaturated, linear or branched hydrocarbon-based group, comprising 6 to 40 and better still from 8 to 30 carbon atoms, which is optionally substituted, in particular, with one or more hydroxyl groups (in particular 1 to 4). If they are unsaturated, these compounds may comprise one to three conjugated or unconjugated carbon-carbon double bonds.

As regards the C6 to C16 liquid hydrocarbons, these may be linear, branched, or optionally cyclic, and are preferably chosen from alkanes. Examples that may be mentioned include hexane, cyclohexane, undecane, dodecane, isododecane, tridecane or isoparaffins, such as isohexadecane or isodecane, and mixtures thereof.

The liquid hydrocarbons comprising more than 16 carbon atoms may be linear or branched, and of mineral or synthetic origin, and are preferably chosen from liquid paraffins or liquid petroleum jelly (or mineral oil), polydecenes, hydrogenated polyisobutene such as Parleam®, and mixtures thereof.

A hydrocarbon-based oil of animal origin that may be mentioned is perhydrosqualene.

The triglyceride oils of plant or synthetic origin are preferably chosen from liquid fatty acid triglycerides including from 6 to 30 carbon atoms, for instance heptanoic or octanoic acid triglycerides, or alternatively, for example, sunflower oil, maize oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stearinerie Dubois or those sold under the names Miglyol® 810, 812 and 818 by the company Dynamit Nobel, jojoba oil and shea butter oil, and mixtures thereof.

As regards the fluoro oils, they may be chosen from perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethylperfluoromorpholine sold under the name PF 5052® by the company 3M.

The liquid fatty alcohols that are suitable for use in the invention are more particularly chosen from linear or branched, saturated or unsaturated alcohols, preferably unsaturated or branched alcohols, including from 6 to 40 carbon atoms and preferably from 8 to 30 carbon atoms. These fatty alcohols are neither oxyalkylenated nor glycerolated. Examples that may be mentioned include octyldodecanol, 2-butyloctanol, 2-hexyldecanol, 2-undecylpentadecanol, isostearyl alcohol, oleyl alcohol, linolenyl alcohol, ricinoleyl alcohol, undecylenyl alcohol and linoleyl alcohol, and mixtures thereof. Preferably, oleyl alcohol will be used.

As regards the liquid esters of fatty acids and/or of fatty alcohols, other than the triglycerides mentioned previously, mention may be made notably of esters of saturated or unsaturated, linear C1 to C26 or branched C3 to C26 aliphatic mono- or polyacids and of saturated or unsaturated, linear C1 to C26 or branched C3 to C26 aliphatic mono- or polyalcohols, the total carbon number of the esters being greater than or equal to 6 and more advantageously greater than or equal to 10.

Preferably, for the esters of monoalcohols, at least one from among the alcohol and the acid is branched.

Among the monoesters, mention may be made of dihydroabietyl behenate; octyldodecyl behenate; isocetyl behenate; isostearyl lactate; lauryl lactate; linoleyl lactate; oleyl lactate; isostearyl octanoate; isocetyl octanoate; octyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; octyl isononanoate; 2-ethylhexyl isononate; octyldodecyl erucate; oleyl erucate; ethyl palmitate, isopropyl palmitate, 2-ethylhexyl palmitate, 2-octyldecyl palmitate; alkyl myristates such as isopropyl 2-octyldodecyl myristate, isobutyl stearate; 2-hexyldecyl laurate, and mixtures thereof.

Preferably, among the monoesters of monoacids and of monoalcohols, use will be made of ethyl palmitate and isopropyl palmitate, alkyl myristates such as isopropyl myristate or ethyl myristate, isocetyl stearate, 2-ethylhexyl isononanoate, isodecyl neopentanoate and isostearyl neopentanoate, and mixtures thereof.

Esters of C4 to C22 dicarboxylic or tricarboxylic acids and of C1 to C22 alcohols and esters of monocarboxylic, dicarboxylic or tricarboxylic acids and of C2 to C26 dihydroxy, trihydroxy, tetrahydroxy or pentahydroxy alcohols may also be used.

Mention may notably be made of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates, and mixtures thereof.

The composition may also comprise, as fatty ester, sugar esters and diesters of C6 to C30 and preferably C12 to C22 fatty acids. It is recalled that the term "sugar" refers to oxygen-bearing hydrocarbon-based compounds bearing several alcohol functions, with or without aldehyde or ketone functions, and which include at least 4 carbon atoms. These sugars may be monosaccharides, oligosaccharides or polysaccharides other than the anionic polysaccharides described hereinbelow.

Examples of suitable sugars that may be mentioned include sucrose, glucose, galactose, ribose, fucose, maltose, fructose, mannose, arabinose, xylose and lactose, and derivatives thereof, notably alkyl derivatives, such as methyl derivatives, for instance methylglucose.

The sugar esters of fatty acids may be chosen notably from the group comprising the esters or mixtures of esters of sugars described above and of linear or branched, saturated or unsaturated C6 to C30 and preferably C12 to C22 fatty acids. If they are unsaturated, these compounds may comprise one to three conjugated or unconjugated carbon-carbon double bonds.

The esters may also be chosen from monoesters, diesters, triesters, tetraesters and polyesters, and mixtures thereof.

These esters may be, for example, oleates, laurates, palmitates, myristates, behenates, cocoates, stearates, linoleates, linolenates, caprates, arachidonates or mixtures thereof notably such as the mixed oleo-palmitate, oleo-stearate and palmito-stearate esters.

More particularly, use is made of monoesters and diesters and notably sucrose, glucose or methylglucose mono- or di-oleates, -stearates, -behenates, -oleopalmitates, -linoleates, -linolenates and -oleostearates, and mixtures thereof.

An example that may be mentioned is the product sold under the name Glucate® DO by the company Amerchol, which is a methylglucose dioleate.

Preferably, use will be made of a liquid ester of a monoacid and of a monoalcohol.

According to one embodiment, the fatty substances other than fatty acids that are useful according to the invention are chosen from liquid fatty substances, preferably from liquid hydrocarbons containing more than 16 carbon atoms, plant oils, liquid fatty alcohols and liquid fatty esters and mixtures thereof, more preferentially from liquid fatty alcohols.

Preferentially, the liquid fatty substance(s) are chosen from liquid fatty alcohols, in particular oleyl alcohol.

The solid fatty substances preferably have a viscosity of greater than 2 Pa·s, measured at 25° C. and at a shear rate of 1 $s^{-1}$.

The solid fatty substance(s) are preferably chosen from solid fatty alcohols, solid esters of fatty acids and/or of fatty alcohols, waxes, ceramides and mixtures thereof.

The term "fatty alcohol" means a long-chain aliphatic alcohol including from 6 to 40 carbon atoms, preferably from 8 to 30 carbon atoms and comprising at least one hydroxyl group OH. These fatty alcohols are neither oxyalkylenated nor glycerolated.

The solid fatty alcohols may be saturated or unsaturated, and linear or branched, and include from 8 to 40 carbon atoms, preferably from 10 to 30 carbon atoms. Preferably, the solid fatty alcohols have the structure R—OH with R denoting a linear alkyl group, optionally substituted with one or more hydroxyl groups, comprising from 8 to 40, preferentially from 10 to 30 carbon atoms, better still from 10 to 30, or even from 12 to 24, atoms and even better still from 14 to 22 carbon atoms.

The solid fatty alcohols that may be used are preferably chosen from saturated or unsaturated, linear or branched, preferably linear and saturated, (mono)alcohols including from 8 to 40 carbon atoms, better still from 10 to 30, or even from 12 to 24, atoms and even better still from 14 to 22 carbon atoms.

The solid fatty alcohols that may be used may be chosen, alone or as a mixture, from: myristyl alcohol (or 1-tetradecanol); cetyl alcohol (or 1-hexadecanol); stearyl alcohol (or 1-octadecanol); arachidyl alcohol (or 1-eicosanol); behenyl alcohol (or 1-docosanol); lignoceryl alcohol (or 1-tetracosanol); ceryl alcohol (or 1-hexacosanol); montanyl alcohol (or 1-octacosanol); myricyl alcohol (or 1-triacontanol).

Preferentially, the solid fatty alcohol is chosen from cetyl alcohol, stearyl alcohol, behenyl alcohol, myristyl alcohol, arachidyl alcohol, and mixtures thereof, such as cetylstearyl alcohol or cetearyl alcohol. Particularly preferably, the solid fatty alcohol is chosen from cetyl alcohol, stearyl alcohol and mixtures thereof such as cetylstearyl alcohol or cetearyl alcohol.

The solid esters of a fatty acid and/or of a fatty alcohol that may be used are preferably chosen from esters derived from a C9-C26 carboxylic fatty acid and/or from a C9-C26 fatty alcohol.

Preferably, these solid fatty esters are esters of a linear or branched, saturated carboxylic acid including at least 10 carbon atoms, preferably from 10 to 30 carbon atoms and more particularly from 12 to 24 carbon atoms, and of a linear or branched, saturated monoalcohol, including at least 10 carbon atoms, preferably from 10 to 30 carbon atoms and more particularly from 12 to 24 carbon atoms. The saturated carboxylic acids may optionally be hydroxylated, and are preferably monocarboxylic acids.

Esters of C4-C22 dicarboxylic or tricarboxylic acids and of C1-C22 alcohols and esters of monocarboxylic, dicarboxylic or tricarboxylic acids and of C2-C26 dihydroxy, trihydroxy, tetrahydroxy or pentahydroxy alcohols may also be used.

Mention may notably be made of octyldodecyl behenate, isocetyl behenate, cetyl lactate, stearyl octanoate, octyl octanoate, cetyl octanoate, decyl oleate, hexyl stearate, octyl stearate, myristyl stearate, cetyl stearate, stearyl stearate, octyl pelargonate, cetyl myristate, myristyl myristate, stearyl myristate, diethyl sebacate, diisopropyl sebacate, diisopropyl adipate, di-n-propyl adipate, dioctyl adipate, dioctyl maleate, octyl palmitate, myristyl palmitate, cetyl palmitate, stearyl palmitate, and mixtures thereof.

Preferably, the solid esters of a fatty acid and/or of a fatty alcohol are chosen from C9-C26 alkyl palmitates, notably myristyl palmitate, cetyl palmitate or stearyl palmitate; C9-C26 alkyl myristates, such as cetyl myristate, stearyl myristate and myristyl myristate; and C9-C26 alkyl stearates, notably myristyl stearate, cetyl stearate and stearyl stearate; and mixtures thereof.

For the purposes of the present invention, a wax is a lipophilic compound, which is solid at 25° C. and atmospheric pressure, with a reversible solid/liquid change of state, having a melting point greater than about 40° C., which may be up to 200° C., and having in the solid state anisotropic crystal organization. In general, the size of the wax crystals is such that the crystals diffract and/or scatter light, giving the composition that comprises them a more or less opaque cloudy appearance. By bringing the wax to its melting point, it is possible to make it miscible with oils and to form a microscopically homogeneous mixture, but on returning the temperature of the mixture to room temperature, recrystallization of the wax, which is microscopically and macroscopically detectable (opalescence), is obtained.

In particular, the waxes that are suitable for use in the invention may be chosen from waxes of animal, plant or mineral origin, non-silicone synthetic waxes, and mixtures thereof.

Mention may be made notably of hydrocarbon-based waxes, for instance beeswax, notably of organic origin, lanolin wax and Chinese insect waxes; rice bran wax, carnauba wax, candelilla wax, ouricury wax, esparto grass wax, berry wax, shellac wax, Japan wax and sumac wax; montan wax, orange wax and lemon wax, microcrystalline waxes, paraffins and ozokerite; polyethylene waxes, the waxes obtained by Fischer-Tropsch synthesis and waxy copolymers, and also esters thereof.

Mention may also be made of C20 to C60 microcrystalline waxes, such as Microwax HW. Mention may also be made of the MW 500 polyethylene wax sold under the reference Permalen 50-L polyethylene.

Mention may also be made of the waxes obtained by catalytic hydrogenation of animal or plant oils containing linear or branched C8 to C32 fatty chains. Among these waxes mention may notably be made of isomerized jojoba oil such as the trans-isomerized partially hydrogenated jojoba oil, notably the product manufactured or sold by the company Desert Whale under the commercial reference Iso-Jojoba-50®, hydrogenated sunflower oil, hydrogenated castor oil, hydrogenated coconut kernel oil, hydrogenated lanolin oil and bis(1,1,1-trimethylolpropane) tetrastearate, notably the product sold under the name Hest 2T-4S® by the company Heterene.

The waxes obtained by hydrogenation of castor oil esterified with cetyl alcohol, such as those sold under the names Phytowax Castor 16L64® and 22L73® by the company Sophim, may also be used.

A wax that may also be used is a C20-C40 alkyl (hydroxystearyloxy)stearate (the alkyl group containing from 20 to 40 carbon atoms), alone or as a mixture. Such a wax is notably sold under the names Kester Wax K 82 P®, Hydroxypolyester K 82 P® and Kester Wax K 80 P® by the company Koster Keunen.

It is also possible to use microwaxes in the compositions of the invention; mention may notably be made of carnauba microwaxes, such as the product sold under the name MicroCare 350® by the company Micro Powders, synthetic-wax microwaxes, such as the product sold under the name MicroEase 114S® by the company Micro Powders, microwaxes constituted of a mixture of carnauba wax and polyethylene wax, such as the products sold under the names Micro Care 300® and 310® by the company Micro Powders, microwaxes constituted of a mixture of carnauba wax and of synthetic wax, such as the product sold under the name Micro Care 325® by the company Micro Powders, polyethylene microwaxes, such as the products sold under the names Micropoly 200®, 220®, 220L® and 250S® by the company Micro Powders, and polytetrafluoroethylene microwaxes, such as the products sold under the names Microslip 519® and 519 L® by the company Micro Powders.

The waxes are preferably chosen from mineral waxes, for instance paraffin, petroleum jelly, lignite or ozokerite wax; plant waxes, for instance cocoa butter or cork fibre or sugar cane waxes, olive tree wax, rice wax, hydrogenated jojoba wax, ouricury wax, carnauba wax, candelilla wax, esparto grass wax, or absolute waxes of flowers, such as the essential wax of blackcurrant blossom sold by the company Bertin (France); waxes of animal origin, for instance beeswaxes or modified beeswaxes (cera bellina), spermaceti, lanolin wax and lanolin derivatives; microcrystalline waxes; and mixtures thereof.

The ceramides, or ceramide analogues such as glycoceramides, which may be used in the compositions according to the invention, are known; mention may be made in particular of ceramides of classes I, II, III and V according to the Dawning classification.

The ceramides or analogues thereof that may be used preferably correspond to the following formula: $R^3CH(OH)CH(CH_2OR^2)(NHCOR^1)$, in which:

- $R^1$ denotes a linear or branched, saturated or unsaturated alkyl group, derived from $C_{14}$-$C_{30}$ fatty acids, it being possible for this group to be substituted with a hydroxyl group in the alpha position, or a hydroxyl group in the omega position esterified with a saturated or unsaturated $C_{16}$-$C_{30}$ fatty acid;
- $R^2$ denotes a hydrogen atom, a (glycosyl)n group, a (galactosyl)m group or a sulfogalactosyl group, in which n is an integer ranging from 1 to 4 and m is an integer ranging from 1 to 8;
- $R^3$ denotes a $C_{15}$-$C_{26}$ hydrocarbon-based group, saturated or unsaturated in the alpha position, this group possibly being substituted with one or more $C_1$-$C_{14}$ alkyl groups; it being understood that in the case of natural ceramides or glycoceramides, $R^3$ may also denote a $C_{15}$-$C_{26}$ alpha-hydroxyalkyl group, the hydroxyl group being optionally esterified with a $C_{16}$-$C_{30}$ alpha-hydroxy acid.

The ceramides that are more particularly preferred are the compounds for which $R^1$ denotes a saturated or unsaturated alkyl derived from $C_{16}$-$C_{22}$ fatty acids; $R^2$ denotes a hydrogen atom and $R^3$ denotes a saturated linear $C_{15}$ group.

Preferentially, use is made of ceramides for which $R^1$ denotes a saturated or unsaturated alkyl group derived from $C_{14}$-$C_{30}$ fatty acids; $R^2$ denotes a galactosyl or sulfogalactosyl group; and $R^3$ denotes a $-CH{=}CH-(CH_2)_{12}-CH_3$ group.

Use may also be made of compounds for which $R^1$ denotes a saturated or unsaturated alkyl radical derived from $C_{12}$-$C_{22}$ fatty acids; $R^2$ denotes a galactosyl or sulfogalactosyl radical and $R^3$ denotes a saturated or unsaturated $C_{12}$-$C_{22}$ hydrocarbon-based radical and preferably a $-CH{=}CH-(CH_2)_{12}-CH_3$ group.

As compounds that are particularly preferred, mention may also be made of 2-N-linoleoylaminooctadecane-1,3-diol; 2-N-oleoylaminooctadecane-1,3-diol; 2-N-palmitoylaminooctadecane-1,3-diol; 2-N-stearoylaminooctadecane-1,3-diol; 2-N-behenoylaminooctadecane-1,3-diol; 2-N-[2-hydroxypalmitoyl]aminooctadecane-1,3-diol; 2-N-stearoylaminooctadecane-1,3,4-triol and in particular N-stearoylphytosphingosine, 2-N-palmitoylaminohexadecane-1,3-diol, N-linoleoyldihydrosphingosine, N-oleoyldihydrosphingosine, N-palmitoyldihydrosphingosine, N-stearoyldihydrosphingosine, and N-behenoyldihydrosphingosine, N-docosanoyl-N-methyl-D-glucamine, cetylic acid N-(2-hydroxyethyl)-N-(3-cetyloxy-2-hydroxypropyl)amide and bis(N-hydroxyethyl-N-cetyl)malonamide; and mixtures thereof. N-Oleoyldihydrosphingosine will preferably be used.

The solid fatty substances are preferably chosen from solid fatty alcohols, in particular from cetyl alcohol, stearyl alcohol and mixtures thereof such as cetylstearyl alcohol or cetearyl alcohol.

Butters may also be used.

For the purposes of the present invention, the term "butter" (also referred to as a "pasty fatty substance") means a lipophilic fatty compound with a reversible solid/liquid change of state, including at a temperature of 25° C. and at atmospheric pressure (760 mmHg) a liquid fraction and a solid fraction. Preferably, the butter(s) according to the invention have a melting start temperature of more than 25° C. and a melting end temperature of less than 60° C.

Preferably, the particular butter(s) are of plant origin, such as those described in *Ullmann's Encyclopedia of Industrial Chemistry* ("Fats and Fatty Oils", A. Thomas, published online: 15 Jun. 2000, DOI: 10.1002/14356007.a10_173, point 13.2.2.2. Shea Butter, Borneo Tallow, and Related Fats (Vegetable Butters)).

Mention may be made more particularly of shea butter, Karite Nilotica butter (*Butyrospermum parki*), galam butter, (*Butyrospermum parki*), Borneo butter or fat or tengkawang tallow (*Shorea stenoptera*), shorea butter, illipe butter, madhuca butter or *Bassia madhuca longifolia* butter, mowrah butter (*Madhuca latifolia*), katiau butter (*Madhuca mottleyana*), phulwara butter (*M. butyracea*), mango butter (*Mangifera indica*), murumuru butter (*Astrocaryum murumuru*), kokum butter (*Garcinia indica*), ucuuba butter (*Virola sebifera*), tucuma butter, painya butter (*Kpangnan*) (*Pentadesma butyracea*), coffee butter (*Coffea arabica*), apricot butter (*Prunus armeniaca*), macadamia butter (*Macadamia ternifolia*), grapeseed butter (*Vitis vinifera*), avocado butter (*Persea gratissima*), olive butter (*Olea europaea*), sweet almond butter (*Prunus amygdalus dulcis*), cocoa butter and sunflower butter.

An example of a preferred butter is shea butter.

In a known manner, shea butter is extracted from the fruit (also called "kernels" or "nuts") of the *Butyrospemum parkii* tree. Each fruit contains between 45% and 55% fatty substance, which is generally extracted and refined.

According to one preferred embodiment, the fatty substances other than fatty acids that are useful according to the invention are chosen from solid fatty substances, preferably from solid fatty alcohols.

The total content of the fatty substance(s) other than fatty acids preferably ranges from 5% to 30% by weight, more preferentially from 8% to 25% by weight and better still from 10% to 20% by weight, relative to the total weight of the composition.

In one particular embodiment, the composition according to the invention comprises one or more solid fatty substances other than fatty acids, the total content of the solid fatty substance(s) other than fatty acids preferably ranging from 5% to 30% by weight, more preferentially from 8% to 25% by weight and better still from 10% to 20% by weight, relative to the total weight of the composition.

In another particular embodiment, the composition according to the invention comprises one or more liquid fatty substances other than fatty acids, the total content of the liquid fatty substance(s) other than fatty acids preferably ranging from 0.5% to 15% by weight, more preferentially from 1% to 10% by weight and better still from 2% to 5% by weight, relative to the total weight of the composition.

According to one preferred embodiment, the composition according to the invention comprises one or more solid fatty substances other than fatty acids, preferably chosen from solid fatty alcohols and one or more liquid fatty substances other than fatty acids, preferably chosen from liquid fatty alcohols.

Surfactants

The composition according to the present invention may comprise one or more surfactants. These surfactants may be chosen from anionic surfactants, nonionic surfactants and cationic surfactants and/or mixtures thereof.

Preferably, the composition according to the present invention comprises one or more surfactants.

The term "anionic surfactant" means a surfactant including, as ionic or ionizable groups, only anionic groups. These anionic groups are preferably chosen from the following groups: $CO_2H$, $CO_2^-$, $SO_3H$, $SO_3^-$, $OSO_3H$, $OSO_3^-$, $H_2PO_3$, $HPO_3^-$, $PO_3^{2-}$, $H_2PO_2$, $HPO_2^-$, $PO_2^{2-}$, POH and $PO^-$.

As examples of anionic surfactants that can be used in the composition according to the invention, mention may be made of alkyl sulfates, alkyl ether sulfates, alkylamido ether sulfates, alkylaryl polyether sulfates, monoglyceride sulfates, alkyl sulfonates, alkylamide sulfonates, alkylaryl sulfonates, α-olefin sulfonates, paraffin sulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates and N—($C_1$-$C_4$)alkyl N-acyl taurates, salts of alkyl monoesters of polyglycoside-polycarboxylic acids, acyl lactylates, salts of D-galactoside uronic acids, salts of alkyl ether carboxylic acids, salts of alkylaryl ether carboxylic acids, salts of alkylamido ether carboxylic acids; fatty acid salts, and the corresponding non-salified forms of all these compounds; the alkyl and acyl groups of all these compounds (unless specified otherwise) generally including from 6 to 24 carbon atoms and the aryl group generally denoting a phenyl group.

These compounds may be oxyethylenated and then preferably include from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, they may be chosen from alkali metal salts such as the sodium or potassium salt and preferably the sodium salt, ammonium salts, amine salts and in particular amino alcohol salts or alkaline-earth metal salts such as the magnesium salt.

Examples of amino alcohol salts that may notably be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

The anionic surfactants that may be present may be mild anionic surfactants, i.e. anionic surfactants not bearing a sulfate function.

As regards the mild anionic surfactants, mention may be made in particular of the following compounds and salts thereof, and also mixtures thereof: polyoxyalkylenated alkyl ether carboxylic acids, polyoxyalkylenated alkylaryl ether carboxylic acids, polyoxyalkylenated alkylamido ether carboxylic acids, in particular those including 2 to 50 ethylene oxide groups, alkyl D-galactoside uronic acids, acyl sarcosinates, acyl glutamates and alkylpolyglycoside carboxylic esters.

Use may be made most particularly of polyoxyalkylenated carboxylic acid alkyl ethers, for instance carboxylic acid lauryl ether (4.5 OE) sold, for example, under the name Akypo RLM 45 CA from Kao.

The anionic surfactants that may be present may be carboxylic acids comprising at least 8 carbon atoms, also known as fatty acids, optionally in salified form.

For the purposes of the present invention, the term "fatty acid" means an acid comprising at least one linear or branched, saturated or unsaturated hydrocarbon-based chain, such as an alkyl or alkenyl chain, including at least 6 carbon atoms, preferably from 8 to 24 carbon atoms, and better still from 10 to 22 carbon atoms.

The carboxylic acids comprising at least 6 carbon atoms (or fatty acids) according to the invention are neither (poly)oxyalkylenated, nor (poly)glycerolated; in particular, they are neither (poly)oxyethylenated, nor (poly)oxypropylenated.

They preferably have the structure R—COOH in which R denotes a linear or branched $C_7$-$C_{29}$, preferably $C_9$-$C_{23}$ and better still $C_9$-$C_{17}$ alkyl or alkenyl group.

Preferably, the fatty acid according to the invention is chosen from linear fatty acids, better still from unsaturated linear $C_{10}$-$C_{22}$ and notably $C_{10}$-$C_{18}$ fatty acids (R is a linear $C_9$-$C_{23}$ or even $C_9$-$C_{17}$ alkenyl).

Mention may notably be made of oleic, linoleic, linolenic and undecylenic acids, and mixtures thereof. Preferably, oleic acid will be used.

Among the anionic surfactants mentioned above, fatty acids are preferably used.

The nonionic surfactant(s) that may be used in the composition of the present invention are notably described, for example, in the "Handbook of Surfactants" by M. R. Porter, published by Blackie & Son (Glasgow and London), 1991, pages 116-178.

Examples of nonionic surfactants that may be mentioned include the following compounds, alone or as a mixture:

oxyalkylenated ($C_8$-$C_2$)alkylphenols;

saturated or unsaturated, linear or branched, oxyalkylenated or glycerolated $C_8$-$C_{40}$ alcohols, preferably including one or two fatty chains; distinct from the fatty alcohols described in the "fatty substances" section;

saturated or unsaturated, linear or branched, oxyalkylenated $C_8$ to $C_{30}$ fatty acid amides;

esters of saturated or unsaturated, linear or branched, $C_8$-$C_{30}$ acids and of polyethylene glycols;

preferably oxyethylenated esters of saturated or unsaturated, linear or branched, $C_8$ to $C_{30}$ acids and of sorbitol;

fatty acid esters of sucrose;

($C_5$-$C_{30}$)alkyl(poly)glucosides, ($C_5$-$C_{30}$)alkenyl(poly)glucosides, which are optionally oxyalkylenated (0 to 10 oxyalkylene units) and comprising from 1 to 15 glucose units, ($C_8$-$C_{30}$)alkyl(poly)glucoside esters;

saturated or unsaturated oxyethylenated plant oils;

condensates of ethylene oxide and/or of propylene oxide;

N—($C_8$-$C_{30}$)alkylglucamine and N—($C_8$-$C_{30}$)acylmethylglucamine derivatives;

amine oxides.

They are notably chosen from alcohols distinct from the fatty alcohols described in the "fatty substances" section, α-diols and ($C_1$-$C_{20}$)alkylphenols, these compounds being ethoxylated, propoxylated or glycerolated and containing at least one fatty chain including, for example, from 8 to 18 carbon atoms, the number of ethylene oxide or propylene oxide groups possibly ranging notably from 1 to 200, and the number of glycerol groups possibly ranging notably from 1 to 30.

Mention may also be made of condensates of ethylene oxide and of propylene oxide with fatty alcohols, ethoxylated fatty amides preferably containing from 1 to 30 ethylene oxide units, polyglycerolated fatty amides including on average from 1 to 5, and in particular from 1.5 to 4, glycerol groups, ethoxylated fatty acid esters of sorbitan containing from 1 to 30 ethylene oxide units, fatty acid esters of sucrose, fatty acid esters of polyethylene glycol, ($C_6$-$C_{24}$ alkyl)polyglycosides, oxyethylenated plant oils, N—($C_6$-$C_{24}$ alkyl)glucamine derivatives, amine oxides such as ($C_{10}$-$C_{14}$ alkyl)amine oxides or N—($C_{10}$-$C_{14}$ acyl)aminopropylmorpholine oxides.

The $C_8$-$C_{30}$ and preferably $C_{12}$-$C_{22}$ fatty acid esters (notably monoesters, diesters and triesters) of sorbitan may be chosen from:

- sorbitan caprylate; sorbitan cocoate; sorbitan isostearate; sorbitan laurate; sorbitan oleate; sorbitan palmitate; sorbitan stearate; sorbitan diisostearate; sorbitan dioleate; sorbitan distearate; sorbitan sesquicaprylate; sorbitan sesquiisostearate; sorbitan sesquioleate; sorbitan sesquistearate; sorbitan triisostearate; sorbitan trioleate; and sorbitan tristearate.

The polyoxyethylenated $C_8$-$C_{30}$ (preferably $C_{12}$-$C_{18}$) fatty acid esters (notably monoesters, diesters and triesters) of sorbitan notably containing from 2 to 20 mol of ethylene oxide may be chosen from polyoxyethylenated esters of $C_{12}$-$C_{18}$ fatty acids, in particular lauric, myristic, cetylic or stearic acid, and of sorbitan notably containing from 2 to 30 mol of ethylene oxide, such as:

- polyoxyethylenated sorbitan monolaurate (4 OE) (Polysorbate-21),
- polyoxyethylenated sorbitan monolaurate (20 OE) (Polysorbate-20),
- polyoxyethylenated sorbitan monopalmitate (20 OE) (Polysorbate-40),
- polyoxyethylenated sorbitan monostearate (20 OE) (Polysorbate-60),
- polyoxyethylenated sorbitan monostearate (4 OE) (Polysorbate-61),
- polyoxyethylenated sorbitan monooleate (20 OE) (Polysorbate-80),
- polyoxyethylenated sorbitan monooleate (5 OE) (Polysorbate-81),
- polyoxyethylenated sorbitan tristearate (20 OE) (Polysorbate-65),
- polyoxyethylenated sorbitan trioleate (20 OE) (Polysorbate-85).

The polyoxyethylenated $C_8$-$C_{30}$ (preferably $C_{12}$-$C_{18}$) fatty acid esters (notably monoesters, diesters, triesters and tetraesters) of sorbitan, notably containing from 2 to 20 mol of ethylene oxide, may be chosen from polyoxyethylenated esters, notably containing from 2 to 20 mol of ethylene oxide, such as of $C_{12}$-$C_{18}$ fatty acids, in particular lauric, myristic, cetylic or stearic acid, and of sorbitan, such as:

- the ester polyoxyethylenated with 20 OE of sorbitan and of cocoic acid (PEG-20 sorbitan cocoate);
- the polyoxyethylenated esters (notably containing from 2 to 20 OE) of sorbitan and of isostearic acid (such as PEG-2 sorbitan isostearate; PEG-5 sorbitan isostearate; PEG-20 sorbitan isostearate such as the product sold under the name Nikkol TI 10 V by the company Nikkol),
- the polyoxyethylenated esters (notably containing from 2 to 20 OE) of sorbitan and of lauric acid (such as PEG-10 sorbitan laurate),
- the polyoxyethylenated esters (notably containing from 2 to 20 OE) of sorbitan and of oleic acid containing 10 oxyethylene groups (such as PEG-6 sorbitan oleate; PEG-20 sorbitan oleate),
- the polyoxyethylenated esters (notably containing from 3 to 20 OE) of sorbitan and of stearic acid (such as PEG-3 sorbitan stearate; PEG-4 sorbitan stearate; PEG-6 sorbitan stearate).

The nonionic surfactant(s) are preferably chosen from ethoxylated $C_8$-$C_{24}$ fatty alcohols comprising from 1 to 200 ethylene oxide groups, ethoxylated $C_8$-$C_{30}$ fatty acid esters of sorbitan containing from 1 to 30 ethylene oxide units, ($C_6$-$C_{24}$ alkyl)polyglycosides, and mixtures thereof, better still from ($C_6$-$C_{24}$ alkyl)polyglycosides, even better still from ($C_6$-$C_{24}$ alkyl)polyglycosides such as: coco glucoside, caprylyl/capryl glucoside, lauryl glucoside, decyl glucoside and cetearyl glucoside.

The cationic surfactant(s) that may be used in the composition according to the invention are generally chosen from optionally polyoxyalkylenated primary, secondary or tertiary fatty amines, quaternary ammonium salts, and mixtures thereof.

The fatty amines generally comprise at least one $C_8$-$C_{30}$ hydrocarbon-based chain. Among the fatty amines that may be used according to the invention, examples that may be mentioned include stearylamidopropyldimethylamine and distearylamine.

Examples of quaternary ammonium salts that may notably be mentioned include:

those corresponding to the general formula (X) below:

(X)

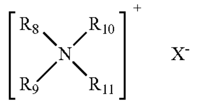

in which the groups $R_8$ to $R_{11}$, which may be identical or different, represent a linear or branched aliphatic group including from 1 to 30 carbon atoms, or an aromatic group such as aryl or alkylaryl, at least one of the groups $R_8$ to $R_{11}$ including from 8 to 30 carbon atoms and preferably from 12 to 24 carbon atoms. The aliphatic groups may include heteroatoms notably such as oxygen, nitrogen, sulfur and halogens.

The aliphatic groups are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates and ($C_1$-$C_4$)alkylsulfonates or ($C_1$-$C_4$)alkylarylsulfonates.

Among the quaternary ammonium salts of formula (X), preference is given, firstly, to tetraalkylammonium chlorides, for instance dialkyldimethylammonium or alkyltrimethylammonium chlorides in which the alkyl group includes from about 12 to 22 carbon atoms, in particular behenyltrimethylammonium chloride, distearyldimethylammonium chloride, cetyltrimethylammonium chloride or benzyldimethylstearylammonium chloride, or, secondly, to distearoylethylhydroxyethylmethylammonium methosulfate, dipalmitoylethylhydroxyethylammonium methosulfate or distearoylethylhydroxyethylammonium methosulfate, or also, finally, to palmitylamidopropyltrimethylammonium chloride or stearamidopropyldimethyl(myristyl acetate)ammonium chloride, sold under the name Ceraphyl® 70 by the company Van Dyk;

- quaternary ammonium salts of imidazoline, for instance those of formula (XI) below:

(XI)

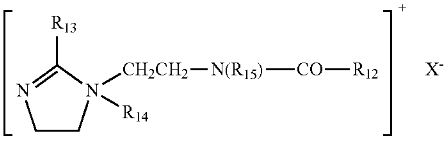

in which R12 represents an alkenyl or alkyl group including from 8 to 30 carbon atoms, for example tallow fatty acid derivatives, R13 represents a hydrogen atom, a $C_1$-$C_4$ alkyl group or an alkenyl or alkyl group including from 8 to 30 carbon atoms, R14 represents a $C_1$-$C_4$ alkyl group, R15 represents a hydrogen atom or a $C_1$-$C_4$ alkyl group, and $X^-$ is an anion chosen from the group of halides, phosphates, acetates, lactates, ($C_1$-$C_4$)alkyl sulfates, and ($C_1$-$C_4$)alkylsulfonates or ($C_1$-$C_4$)alkylarylsulfonates.

Preferably, R12 and R13 denote a mixture of alkenyl or alkyl groups including from 12 to 21 carbon atoms, for example tallow fatty acid derivatives, R14 denotes a methyl group and R15 denotes a hydrogen atom. Such a product is sold, for example, under the name Rewoquat® W 75 by the company Rewo, quaternary diammonium or triammonium salts, in particular of formula (XII) below:

(XII)

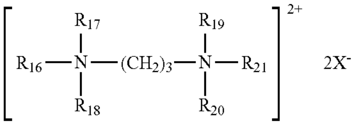

in which R16 denotes an alkyl group including approximately from 16 to 30 carbon atoms, which is optionally hydroxylated and/or interrupted with one or more oxygen atoms; R17 is chosen from hydrogen, an alkyl group including from 1 to 4 carbon atoms or a group —$(CH_2)_3$—$N^+$(R16a)(R17a)(R18a), R16a, R17a, R18a, R18, R19, R20 and R21, which may be identical or different, are chosen from hydrogen or an alkyl group including from 1 to 4 carbon atoms, and X— is an anion chosen from the group of halides, acetates, phosphates, nitrates, ($C_1$-$C_4$)alkyl sulfates, ($C_1$-$C_4$)alkylsulfonates or ($C_1$-$C_4$)alkylarylsulfonates, in particular methyl sulfate and ethyl sulfate.

Such compounds are, for example, Finquat CT-P, sold by the company Finetex (Quaternium 89), and Finquat CT, sold by the company Finetex (Quaternium 75);

quaternary ammonium salts containing one or more ester functions, for instance those of formula (XIII) below:

(XIII)

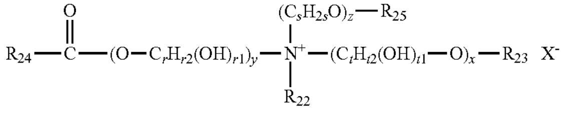

in which: R22 is chosen from $C_1$-$C_6$ alkyl groups and $C_1$-$C_6$ hydroxyalkyl or dihydroxyalkyl groups; R23 is chosen from: the group —C(O)R26, linear or branched, saturated or unsaturated $C_1$-$C_{22}$ hydrocarbon-based groups R27, or a hydrogen atom; R25 is chosen from: the group —C(O)R28, linear or branched, saturated or unsaturated $C_1$-$C_6$ hydrocarbon-based groups R29, or a hydrogen atom; R24, R26 and R28, which may be identical or different, are chosen from linear or branched, saturated or unsaturated $C_7$-$C_{21}$ hydrocarbon-based groups; r, s and t, which may be identical or different, are integers from 2 to 6; r1 and t1, which may be identical or different, are 0 or 1; r2+r1=2 r and t1+t2=2 t, y is an integer from 1 to 10, x and z, which may be identical or different, are integers from 0 to 10, X— is an organic or inorganic simple or complex anion, with the proviso that the sum x+y+z is from 1 to 15, that when x is 0, R23 denotes R27 and that when z is 0, R25 denotes R29.

The alkyl groups R22 may be linear or branched, and more particularly linear.

Preferably, R22 denotes a methyl, ethyl, hydroxyethyl or dihydroxypropyl group, and more particularly a methyl or ethyl group.

Advantageously, the sum x+y+z is from 1 to 10.

When R23 is a hydrocarbon-based group R27, it may be long and may contain 12 to 22 carbon atoms, or may be short and may contain from 1 to 3 carbon atoms.

When R25 is a hydrocarbon-based group R29, it preferably contains 1 to 3 carbon atoms.

Advantageously, R24, R26 and R28, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anion $X^-$ is preferably a halide, preferably chloride, bromide or iodide, a ($C_1$-$C_4$)alkyl sulfate or a ($C_1$-$C_4$)alkyl- or ($C_1$-$C_4$)alkylaryl-sulfonate. However, use may be made of methanesulfonate, phosphate, nitrate, tosylate, an anion derived from an organic acid, such as acetate or lactate, or any other anion that is compatible with the ammonium bearing an ester function.

The anion $X^-$ is even more particularly chloride, methyl sulfate or ethyl sulfate.

Use is made more particularly, in the composition according to the invention, of the ammonium salts of formula (XIII) in which: R22 denotes a methyl or ethyl group, x and y are equal to 1, z is equal to 0 or 1, r, s and t are equal to 2; R23 is chosen from: the group —C(O)R26, methyl, ethyl or $C_{14}$-$C_{22}$ hydrocarbon-based groups, or a hydrogen atom, R25 is chosen from: the group —C(O)R28, or a hydrogen atom, R24, R26 and R28, which may be identical or different, are chosen from linear or branched, saturated or unsaturated C13-C17 hydrocarbon-based groups, and preferably from linear or branched, saturated or unsaturated C13-C17 alkyl and alkenyl groups.

Advantageously, the hydrocarbon-based groups are linear.

Among the compounds of formula (XIII), examples that may be mentioned include salts, notably the chloride or methyl sulfate, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and are derived more particularly from a plant oil such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by quaternization by means of an alkylating agent such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company CECA or Rewoquat® WE 18 by the company Rewo-Witco.

The composition according to the invention may contain, for example, a mixture of quaternary ammonium monoester, diester and triester salts with a weight majority of diester salts.

Use may also be made of the ammonium salts containing at least one ester function that are described in patents U.S. Pat. Nos. 4,874,554 and 4,137,180.

Use may also be made of the behenoylhydroxypropyltrimethylammonium chloride sold, for example, by the company Kao under the name Quartamin BTC 131.

Preferably, the ammonium salts containing at least one ester function contain two ester functions.

Among the cationic surfactants, it is more particularly preferred to choose cetyltrimethylammonium, behenyltrimethylammonium and dipalmitoylethylhydroxyethyl-methylammonium salts, and mixtures thereof, and more particularly behenyl-trimethylammonium chloride, cetyltrimethylammonium chloride, and dipalmitoylethylhydroxyethylammonium methosulfate, and mixtures thereof.

Preferably, the surfactant(s) are chosen from anionic surfactants, nonionic surfactants and mixtures thereof, preferentially from fatty acids, ethoxylated $C_8$-$C_{24}$ fatty alcohols comprising from 1 to 200 ethylene oxide groups, ethoxylated $C_8$-$C_{30}$ fatty acid esters of sorbitan containing from 1 to 30 ethylene oxide units, ($C_6$-$C_{24}$ alkyl)polyglycosides, and mixtures thereof.

More preferentially, the surfactant(s) are chosen from fatty acids, ($C_6$-$C_{24}$ alkyl)polyglycosides and mixtures thereof.

When the composition comprises one or more surfactants, the total content of surfactant(s) in the composition preferably ranges from 0.01% to 15% by weight, more preferentially from 0.1% to 10% by weight, better still from 0.5% to 8% by weight, even better still from 1% to 6% by weight, relative to the total weight of the composition.

When the composition comprises one or more surfactants chosen from fatty acids, the total content of fatty acids in the composition preferably ranges from 0.01% to 15% by weight, more preferentially from 0.1% to 10% by weight, better still from 0.5% to 8% by weight, even better still from 1% to 6% by weight, relative to the total weight of the composition.

When the composition comprises one or more surfactants chosen from ($C_6$-$C_{24}$ alkyl)polyglycosides, the total content of ($C_6$-$C_{24}$ alkyl)polyglycosides in the composition preferably ranges from 0.01% to 15% by weight, more preferentially from 0.1% to 10% by weight, better still from 0.5% to 8% by weight, even better still from 1% to 6% by weight, relative to the total weight of the composition.

Oxidation Base

The composition according to the invention may also comprise one or more oxidation bases, salts thereof, solvates thereof and/or solvates of the salts thereof, and mixtures thereof.

Preferably, the composition according to the invention comprises one or more oxidation bases.

The oxidation bases may be present in the form of salts, solvates and/or solvates of salts.

The addition salts of the oxidation bases present in the composition according to the invention are notably chosen from the addition salts with an acid, such as the hydrochlorides, hydrobromides, sulfates, citrates, succinates, tartrates, lactates, tosylates, benzenesulfonates, methanesulfonates, phosphates and acetates, and the addition salts with a base such as sodium hydroxide, potassium hydroxide, aqueous ammonia, amines or alkanolamines.

Moreover, the solvates of the oxidation bases more particularly represent the hydrates of said oxidation bases and/or the combination of said oxidation bases with a linear or branched $C_1$ to $C_4$ alcohol such as methanol, ethanol, isopropanol or n-propanol. Preferably, the solvates are hydrates.

By way of example, the oxidation bases are chosen from para-phenylenediamines, bis(phenyl)alkylenediamines, para-aminophenols ortho-aminophenols, heterocyclic bases, the addition salts thereof, the solvates thereof and solvates of salts thereof.

Among the para-phenylenediamines that may be mentioned are, for example, para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(p-hydroxyethyl)amino-2-chloroaniline, 2-p-hydroxyethyl-para-phenylenediamine, 2-methoxymethyl-para-phenylenediamine, 2-fluoro-para-phenylenediamine, 2-isopropyl-para-phenylenediamine, N-(β-hydroxypropyl)-para-phenylenediamine, 2-(γ-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the corresponding addition salts, solvates and/or solvates of salts thereof.

Among the para-phenylenediamines mentioned above, particular preference is given to para-phenylenediamine, para-toluenediamine, 2-isopropyl-para-phenylenediamine, 2-β-hydroxyethyl-para-phenylenediamine, 2-(γ-hydroxypropyl)-para-phenylenediamine, 2-methoxymethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-paraphenylenediamine, 2-chloro-para-phenylenediamine and 2-β-acetylaminoethyloxy-para-phenylenediamine, and the corresponding addition salts, solvates and/or solvates of salts thereof.

Among the bis(phenyl)alkylenediamines that may be mentioned, for example, are N,N'-bis(β-hydroxyethyl)-N, N'-bis(4'-aminophenyl)-1,3-diaminopropanol, N,N'-bis(p-hydroxyethyl)-N,N'-bis(4'-aminophenyl)ethylenediamine, N,N'-bis(4-aminophenyl)tetramethylenediamine, N,N'-bis (β-hydroxyethyl)-N,N'-bis(4-aminophenyl)tetramethylene-diamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the corresponding addition salts, the solvates and solvates of the salts.

Among the para-aminophenols that are mentioned are, for example, para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(3-hydroxyethylaminomethyl)phenol and 4-amino-2-fluorophenol, the corresponding addition salts, the solvates and solvates of the salts.

Among the ortho-aminophenols that may be mentioned, for example, are 2-aminophenol, 2-amino-5-methylphenol, 2-amino-6-methylphenol and 5-acetamido-2-aminophenol, the corresponding addition salts, the solvates and solvates of the salts.

Among the heterocyclic bases that may be mentioned, for example, are pyridine, pyrimidine and pyrazole derivatives.

Among the pyridine derivatives that may be mentioned are the compounds described, for example, in patents GB 1 026 978 and GB 1 153 196, for example 2,5-diaminopyridine, 2-(4-methoxyphenyl)amino-3-aminopyridine and 3,4-diaminopyridine, and the corresponding addition salts, the solvates and the solvates of the salts.

Other pyridine oxidation bases that are useful in the present invention are the 3-aminopyrazolo[1,5-a]pyridine oxidation bases or the corresponding addition salts described, for example, in patent application FR 2 801 308. Examples that may be mentioned include pyrazolo[1,5-a] pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a] pyrid-5-yl)ethanol, 2-(3-aminopyrazolo[1,5-a]pyrid-7-yl) ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a] pyrid-5-yl)(2-hydroxyethyl)amino]ethanol, 2-[(3-aminopyrazolo[1,5-a]pyrid-7-yl)(2-hydroxyethyl)amino] ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-p-hydroxyethoxy-3-aminopyrazolo[1,5-a]pyridine and 2-(4-dimethylpiperazinium-1-yl)-3-aminopyrazolo[1,5-a]pyridine, and the corresponding addition salts, the solvates and the solvates of the salts.

More particularly, the oxidation bases that are useful in the present invention are chosen from 3-aminopyrazolo[1, 5-a]pyridines and preferably substituted on carbon atom 2 with:

a) a (di)($C_1$-$C_6$)(alkyl)amino group, said alkyl group possibly being substituted with at least one hydroxyl, amino or imidazolium group;

b) an optionally cationic 5- to 7-membered heterocycloalkyl group containing from 1 to 3 heteroatoms, optionally substituted with one or more ($C_1$-$C_6$)alkyl groups, such as a di($C_1$-$C_4$)alkylpiperazinium group; or c) a ($C_1$-$C_6$)alkoxy group optionally substituted with one or more hydroxyl groups, such as a β-hydroxyalkoxy group, and the corresponding addition salts, the solvates and the solvates of the salts.

Among the pyrimidine derivatives that may be mentioned are the compounds described, for example, in patents DE 2359399; JP 88-169571; JP 05-63124; EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof, the solvates and the solvates of the salts thereof, and the tautomeric forms thereof, when a tautomeric equilibrium exists.

Among the pyrazole derivatives that may be mentioned are the compounds described in patents DE 3843892 and DE 4133957 and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(3-hydroxyethyl)-3-methylpyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl) amino-1-methylpyrazole, and the corresponding addition salts, the solvates and the solvates of the salts. Use may also be made of 4,5-diamino-1-(β-methoxyethyl)pyrazole.

A 4,5-diaminopyrazole will preferably be used and even more preferentially 4,5-diamino-1-(β-hydroxyethyl)pyrazole and/or a corresponding salt, a solvate and/or a solvate of a salt.

The pyrazole derivatives that may also be mentioned comprise diamino-N,N-dihydropyrazolopyrazolones and in particular those described in patent application FR-A-2 886 136, such as the following compounds and the corresponding addition salts: 2,3-diamino-6,7-dihydro-1H,5H-pyrazolo [1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a] pyrazol-1-one, 2-amino-3-(pyrrolidin-1-yl)-6,7-dihydro-1H, 5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-bis(2-hydroxyethyl)-1,2-dihydropyrazol-3-one, 2-amino-3-(2-hydroxyethyl)amino-6,7-dihydro-1H,5H-pyrazolo[1,2-a] pyrazol-1-one, 2-amino-3-dimethylamino-6,7-dihydro-1H, 5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one and 2,3-diamino-6-hydroxy-6,7-dihydro-1H,5H-pyrazolo[1,2-a]pyrazol-1-one, the corresponding addition salts, the solvates thereof and/or the solvates of the salts thereof, and mixtures thereof.

Use will preferably be made of 2,3-diamino-6,7-dihydro-1H,5H-pyrazolo[1,2-a]pyrazol-1-one and/or a corresponding salt, solvate and/or solvate of a salt.

Use will preferably be made, as heterocyclic bases, of 4,5-diamino-1-(3-hydroxyethyl)pyrazole and/or 2,3-diamino-6,7-dihydro-1H,5H-pyrazolo[1,2-a]pyrazol-1-one and/or 2-β-hydroxyethoxy-3-aminopyrazolo[1,5-a]pyridine and/or a corresponding salt, solvate and/or solvate of a salt.

Preferably, the oxidation base(s) are chosen from para-phenylenediamines, bis(phenyl)alkylenediamines, para-aminophenols, ortho-aminophenols, heterocyclic bases, and the corresponding addition salts, the solvates thereof and the solvates of the salts thereof, and mixtures thereof; more preferentially from 2-methoxymethyl-para-phenylenediamine, 2-p-hydroxyethyl-para-phenylenediamine, 2-γ-hydroxypropyl-para-phenylenediamine, and the addition salts thereof, the solvates thereof and/or the solvates of the salts thereof, and mixtures thereof.

When the composition comprises at least one oxidation base, the oxidation base(s) is (are) preferably present in a total content ranging from 0.001% to 20% by weight, preferably from 0.005% to 15% by weight, more preferentially from 0.01% to 10% by weight, better still from 0.05% to 5%, even better still from 0.1% to 3% by weight, relative to the weight of the composition.

According to a preferred embodiment, when the composition comprises at least one oxidation base chosen from 2-methoxymethyl-para-phenylenediamine, 2-β-hydroxyethyl-para-phenylenediamine, 2-γ-hydroxypropyl-para-phenylenediamine, addition salts thereof, solvates thereof and/or solvates of the salts thereof and mixtures thereof, said base(s) is (are) present in a total content ranging from 0.001% to 20% by weight, preferably from 0.005% to 15% by weight, more preferentially from 0.01% to 10% by weight, better still from 0.05% to 5%, even better still from 0.1% to 3% by weight, relative to the total weight of the composition.

In a particular embodiment, the composition according to the invention is free of oxidation bases chosen from para-phenylenediamine, para-toluenediamine, addition salts thereof, solvates thereof and solvates of the salts thereof.

According to a particular embodiment, the composition according to the invention comprises:

- at least one coupler chosen from: 6-hydroxybenzomorpholine of formula (I), the addition salts thereof, the solvates thereof and/or the solvates of the salts thereof, hydroxyethyl-3,4-methylenedioxyaniline of formula (II), the addition salts thereof, the solvates thereof and/or the solvates of the salts thereof, 2-amino-5-ethylphenol of formula (III), the addition salts thereof, the solvates thereof and/or the solvates of the salts thereof, and mixtures thereof;

(I)

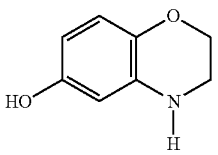

-continued (II)

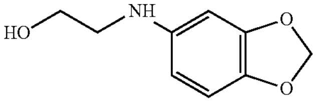

(III)

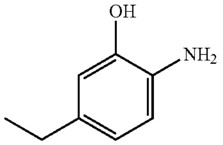

1,3-propanediol;

- at least one alkaline agent preferably chosen from alkanolamines such as monoethanolamine, diethanolamine, triethanolamine; aqueous ammonia, carbonates or bicarbonates such as sodium (hydrogen) carbonate and potassium (hydrogen) carbonate, alkali metal or alkaline-earth metal silicates or metasilicates such as sodium metasilicate, and mixtures thereof, more preferentially from alkanolamines and aqueous ammonia, better still from alkanolamines;
- at least one fatty substance other than fatty acids, preferably chosen from solid fatty substances, more preferentially from solid fatty alcohols, solid esters of fatty acids and/or of fatty alcohols, waxes, ceramides, and more preferentially chosen from solid fatty alcohols;
- at least one surfactant, preferably chosen from fatty acids, ($C_6$-$C_{24}$ alkyl)polyglycosides and mixtures thereof; and
- at least one oxidation base.

Solvents

The composition according to the invention may also comprise at least one organic solvent other than 1,3-propanediol.

Preferably, the composition comprises at least one solvent.

Examples of organic solvents that may be mentioned include linear or branched $C_2$-$C_4$ alkanols, such as ethanol and isopropanol; polyols other than 1,3-propanediol and polyol ethers, for instance 2-butoxyethanol, propylene glycol, dipropylene glycol, propylene glycol monomethyl ether, glycerol, diethylene glycol monomethyl ether and monoethyl ether, and also aromatic alcohols or ethers, for instance benzyl alcohol or phenoxyethanol, and mixtures thereof.

Preferably, the organic solvent(s) is (are) chosen from polyols, more preferentially the organic solvent is glycerol.

The organic solvent(s) other than 1,3-propanediol may be present in an amount ranging from 0.01% to 30% by weight, preferably ranging from 2% to 25% by weight, relative to the total weight of the composition.

In addition, the composition according to the invention is preferably an aqueous composition. The composition preferably comprises water in an amount of greater than or equal to 5% by weight, preferably greater than or equal to 10% by weight, and better still greater than or equal to 15% by weight, relative to the total weight of the composition.

Sequestrants

The composition according to the invention may comprise at least one sequestrant (or chelating agent).

Preferably, the composition according to the invention comprises one or more sequestrants.

The definition of a "sequestrant" (or "chelating agent") is well known to those skilled in the art and refers to a compound or a mixture of compounds that are capable of forming a chelate with a metal ion. A chelate is an inorganic complex in which a compound (the sequestrant or chelating agent) is coordinated to a metal ion, i.e. it forms one or more bonds with the metal ion (formation of a ring including the metal ion).

A sequestrant (or chelating agent) generally comprises at least two electron-donating atoms which enable the formation of bonds with the metal ion.

Within the context of the present invention, the sequestrant(s) may be chosen from carboxylic acids, preferably aminocarboxylic acids, phosphonic acids, preferably aminophosphonic acids, polyphosphoric acids, preferably linear polyphosphoric acids, salts thereof, and derivatives thereof.

The salts are in particular alkali metal, alkaline-earth metal, ammonium and substituted ammonium salts.

The following compounds may be mentioned as examples of chelating agents based on carboxylic acids: diethylenetriaminepentaacetic acid (DTPA), ethylenediaminedisuccinic acid (EDDS) and trisodium ethylenediamine disuccinate such as Octaquest E30 from Octel, ethylenediaminetetraacetic acid (EDTA) and salts thereof such as disodium EDTA, tetrasodium EDTA, ethylenediamine-N,N'-diglutaric acid (EDDG), glycinamide-N,N'-disuccinic acid (GADS), 2-hydroxypropylenediamine-N,N'-disuccinic acid (HPDDS), ethylenediamine-N,N'-bis(ortho-hydroxyphenylacetic acid) (EDDHA), N,N'-bis(2-hydroxybenzyl)ethylenediamine-N,N'-diacetic acid (HBED), nitrilotriacetic acid (NTA), methylglycinediacetic acid (MGDA), N-2-hydroxyethyl-N,N-diacetic acid and glyceryliminodiacetic acid (as described in EP-A-317 542 and EP-A-399 133), iminodiacetic acid-N-2-hydroxypropylsulfonic acid and aspartic acid-N-carboxymethyl-N-2-hydroxypropyl-3-sulfonic acid (as described in EP-A-516 102), beta-alanine-N,N'-diacetic acid, aspartic acid-N,N'-diacetic acid, and aspartic acid-N-monoacetic acid (described in EP-A-509 382), chelating agents based on iminodisuccinic acid (IDSA) (as described in EP-A-509 382), ethanoldiglycine acid, phosphonobutanetricarboxylic acid such as the compound sold by Bayer under the reference Bayhibit AM, N,N-dicarboxymethylglutamic acid and salts thereof such as tetrasodium glutamate diacetate (GLDA) such as Dissolvine GL38 or 45S from AkzoNobel.

The following compounds may be mentioned as examples of chelating agents based on mono- or polyphosphonic acid: diethylenetriaminepenta(methylenephosphonic acid) (DTPMP), ethane-1-hydroxy-1,1,2-triphosphonic acid (E1 HTP), ethane-2-hydroxy-1,1,2-triphosphonic acid (E2HTP), ethane-1-hydroxy-1,1-triphosphonic acid (EHDP), ethane-1,1,2-triphosphonic acid (ETP), ethylenediaminetetramethylenephosphonic acid (EDTMP), hydroxyethane-1,1-diphosphonic acid (HEDP, or etidronic acid), and salts such as disodium etidronate, tetrasodium etidronate.

The following compounds may be mentioned as examples of chelating agents based on polyphosphoric acid: sodium tripolyphosphate (STP), tetrasodium diphosphate, hexametaphosphoric acid, sodium metaphosphate, phytic acid.

According to one embodiment, the sequestrant(s) that are useful according to the invention are phosphorus-based sequestrants, i.e. sequestrants which comprise one or more phosphorus atoms, preferably at least two phosphorus atoms.

The phosphorus-based sequestrant(s) used in the composition according to the invention are preferably chosen from:

- inorganic phosphorus-based derivatives preferably chosen from alkali metal or alkaline-earth metal, preferably alkali metal, phosphates and pyrophosphates, such as sodium pyrophosphate, potassium pyrophosphate, sodium pyrophosphate decahydrate; and alkali metal or alkaline-earth metal, preferably alkali metal, polyphosphates, such as sodium hexametaphosphate, sodium polyphosphate, sodium tripolyphosphate, sodium trimetaphosphate; which are optionally hydrated, and mixtures thereof;
- organic phosphorus-based derivatives, such as organic (poly)phosphates and (poly)phosphonates, such as etidronic acid and/or alkali metal or alkaline-earth metal salts thereof, for instance tetrasodium etidronate, disodium etidronate, and mixtures thereof.

Preferably, the phosphorus-based sequestrant(s) are chosen from linear or cyclic compounds comprising at least two phosphorus atoms bonded together covalently via at least one linker L comprising at least one oxygen atom and/or at least one carbon atom.

The phosphorus-based sequestrant(s) may be chosen from inorganic phosphorus-based derivatives, preferably comprising at least two phosphorus atoms. More preferentially, the phosphorus-based sequestrant(s) are chosen from alkali metal or alkaline-earth metal pyrophosphates, better still from alkali metal pyrophosphates, in particular sodium pyrophosphate (also known as tetrasodium pyrophosphate).

The phosphorus-based sequestrant(s) may be chosen from organic phosphorus-based derivatives, preferably comprising at least two phosphorus atoms. More preferentially, the phosphorus-based sequestrant(s) are chosen from etidronic acid (also known as 1-hydroxyethane-1,1-diphosphonic acid) and/or alkali metal or alkaline-earth metal, preferably alkali metal, salts thereof, for instance tetrasodium etidronate and disodium etidronate.

Thus, preferably, the phosphorus-based sequestrant(s) are chosen from alkali metal pyrophosphates, etidronic acid and/or alkali metal salts thereof, and a mixture of these compounds.

Particularly preferably, the phosphorus-based sequestrant (s) are chosen from tetrasodium etidronate, disodium etidronate, etidronic acid, tetrasodium pyrophosphate, and a mixture of these compounds.

According to the present invention, the sequestrants are preferably chosen from diethylenetriaminepentaacetic acid (DTPA) and salts thereof, diethylenediaminetetraacetic acid (EDTA) and salts thereof, ethylenediaminedisuccinic acid (EDDS) and salts thereof, etidronic acid and salts thereof, N,N-dicarboxymethylglutamic acid and salts thereof (GLDA), and mixtures thereof.

More preferentially, the sequestrant(s) are chosen from N,N-dicarboxymethylglutamic acid and salts thereof (GLDA), and mixtures thereof.

Among the salts of these compounds, the alkali metal salts and notably the sodium or potassium salts are preferred.

When the composition comprises one or more sequestrants, the total content of the sequestrant(s) preferably ranges from 0.001% to 15% by weight, more preferentially from 0.005% to 10% by weight, better still from 0.01% to 8% by weight, even better still from 0.05% to 5% by weight, relative to the total weight of the composition.

Thickening Polymers

The composition according to the invention may comprise at least one thickening polymer, preferably chosen from polysaccharides, more preferentially from anionic polysaccharides. Preferably, the composition according to the invention comprises one or more thickening polymer(s), preferably chosen from polysaccharides, more preferentially from anionic polysaccharides.

The term "polysaccharides" means polymers which contain at least 11 monosaccharide units. Preferentially, the polysaccharides of the invention include between 20 and 100 000 monosaccharide units.

The anionic polysaccharides according to the invention comprise one or more anionic or anionizable groups, and do not comprise any cationic or cationizable groups.

The anionic polysaccharides that are useful according to the invention may be chosen from those derived from the following sugars: glucose; galactose; arabinose; rhamnose; mannose; xylose; fucose; anhydrogalactose; galacturonic acid; glucuronic acid; mannuronic acid; galactose sulfate; anhydrogalactose sulfate.

The anionic polysaccharides may be natural or synthetic.

According to a particular embodiment, the anionic polysaccharides that are useful in the composition according to the invention are chosen from native gums such as:

- tree or shrub exudates, for instance: acacia gum (branched polymer of galactose, arabinose, rhamnose and glucuronic acid); ghatti gum (polymer derived from arabinose, galactose, mannose, xylose and glucuronic acid); karaya gum (polymer derived from galacturonic acid, galactose, rhamnose and glucuronic acid); gum tragacanth (polymer of galacturonic acid, galactose, fucose, xylose and arabinose);
- gums derived from algae, such as: alginates (polymers of mannuronic acid and glucuronic acid); carrageenans and furcellerans (polymers of galactose sulfate and anhydrogalactose sulfate);
- microbial gums such as: xanthan gums (polymer of glucose, mannose acetate, mannose/pyruvic acid and glucuronic acid); gellan gums (polymer of partially acylated glucose, rhamnose and glucuronic acid).

For the purposes of the present invention, the term "microbial gums" means substances synthesized by fermentation of sugars by microorganisms.

According to a preferred embodiment, the anionic polysaccharides that are useful in the composition according to the invention are chosen from anionic gums, better still from anionic microbial gums, more preferentially from xanthan gums.

When they are present, the total content of thickening polymers preferably ranges from 0.01% to 10% by weight relative to the total weight of the composition, preferably from 0.05% to 8% by weight, better still from 0.1% to 5% by weight relative to the total weight of the composition.

When they are present, the total content of anionic polysaccharides as defined previously preferably ranges from 0.01% to 10% by weight relative to the total weight of the composition, preferably from 0.05% to 8% by weight, better still from 0.1% to 5% by weight relative to the total weight of the composition.

When they are included in the composition, the total content of the anionic microbial gums as defined previously preferably ranges from 0.01% to 10% by weight relative to the total weight of the composition, preferably from 0.05% to 5% by weight, better still from 0.1% to 2% by weight relative to the total weight of the composition.

According to a particular embodiment, the composition according to the invention comprises:

- at least one coupler chosen from: 6-hydroxybenzomorpholine of formula (I), the addition salts thereof, the solvates thereof and/or the solvates of the salts thereof, hydroxyethyl-3,4-methylenedioxyaniline of formula (II), the addition salts thereof, the solvates thereof and/or the solvates of the salts thereof, 2-amino-5-ethylphenol of formula (III), the addition salts thereof, the solvates thereof and/or the solvates of the salts thereof, and mixtures thereof;

(I)

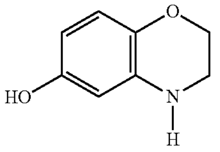

(II)

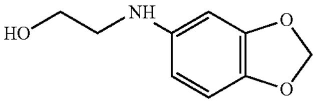

(III)

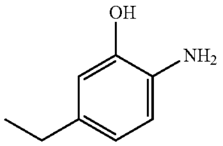

1,3-propanediol;

- at least one alkaline agent preferably chosen from alkanolamines such as monoethanolamine, diethanolamine, triethanolamine; aqueous ammonia, carbonates or bicarbonates such as sodium (hydrogen) carbonate and potassium (hydrogen) carbonate, alkali metal or alkaline-earth metal silicates or metasilicates such as sodium metasilicate, and mixtures thereof, more preferentially from alkanolamines and aqueous ammonia, better still from alkanolamines;
- at least one fatty substance other than fatty acids, preferably chosen from solid fatty substances, more preferentially from solid fatty alcohols, solid esters of fatty acids and/or of fatty alcohols, waxes, ceramides, and more preferentially chosen from solid fatty alcohols;
- at least one surfactant, preferably chosen from fatty acids, ($C_6$-$C_{24}$ alkyl)polyglycosides and mixtures thereof;
- at least one oxidation base;
- at least one sequestrant, preferably chosen from diethylenetriaminepentaacetic acid (DTPA) and salts thereof, diethylenediaminetetraacetic acid (EDTA) and salts thereof, ethylenediaminedisuccinic acid (EDDS) and salts thereof, etidronic acid and salts thereof, N,N-dicarboxymethylglutamic acid and salts thereof (GLDA), and mixtures thereof;
- at least one thickening polymer, preferably chosen from polysaccharides, more preferentially from anionic polysaccharides, better still from anionic microbial gums.

Additives

The composition according to the invention may optionally comprise one or more additives, other than the compounds of the invention and among which mention may be made of cationic, anionic, nonionic or amphoteric polymers or mixtures thereof, other than those mentioned previously, antidandruff agents, anti-seborrhoeic agents, agents for preventing hair loss and/or for promoting hair regrowth, vitamins and provitamins including panthenol, sunscreens, mineral or organic pigments, direct dyes, plasticizers, solubilizers, opacifiers or nacreous agents, antioxidants, hydroxy acids, fragrances, and preserving agents.

Needless to say, a person skilled in the art will take care to select this or these optional additional compounds such that the advantageous properties intrinsically associated with the composition according to the invention are not, or are not substantially, adversely affected by the envisaged addition(s).

The above additives may generally be present in an amount, for each of them, of between 0 and 20% by weight relative to the total weight of the ready-to-use composition.

Preferably, the composition according to the invention does not comprise any chemical oxidizing agents.

Process

The present invention also relates to a process for dyeing keratin fibres, preferably the hair, which comprises the application to said keratin fibres of an effective amount of a composition as defined previously.

The composition may be applied to wet or dry keratin fibres. On conclusion of the treatment, the keratin fibres are optionally rinsed with water, optionally washed with a shampoo and then rinsed with water, before being dried or left to dry.

Preferably, the composition according to the invention comprises at least one oxidizing agent, preferably hydrogen peroxide.

Preferably, the composition according to the invention is mixed at the time of use with a composition comprising at least one chemical oxidizing agent, preferably hydrogen peroxide.

According to this embodiment, at the time of use, the composition according to the invention results from the mixing of at least two compositions:

a dye composition comprising:

one or more oxidation dyes chosen from at least one coupler chosen from: 6-hydroxybenzomorpholine of formula (I), the addition salts thereof, the solvates thereof and/or the solvates of the salts thereof, hydroxyethyl-3,4-methylenedioxyaniline of formula (II), the addition salts thereof, the solvates thereof and/or the solvates of the salts thereof, 2-amino-5-ethylphenol of formula (III), the addition salts thereof, the solvates thereof and/or the solvates of the salts thereof, and mixtures thereof; $NH_2$ (I)

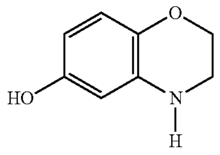

(II)

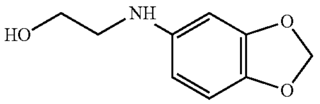

(III)

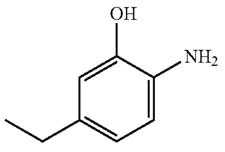

and at least one base chosen from: 2-p-hydroxyethyl-para-phenylenediamine and the addition salts thereof, the solvates thereof and/or the solvates of salts thereof, 2-(γ-hydroxypropyl)-para-phenylenediamine and the addition salts thereof, the solvates thereof and/or the solvates of salts thereof, 2-methoxymethyl-para-phenylenediamine and the addition salts thereof, the solvates thereof and/or the solvates of salts thereof, and mixtures thereof;

1,3-propanediol;

at least one alkaline agent;

at least one fatty substance other than fatty acids, and an oxidizing composition comprising one or more chemical oxidizing agents, preferably hydrogen peroxide.

According to one embodiment, the process according to the invention comprises a step of mixing the composition according to the invention with an oxidizing composition comprising at least one chemical oxidizing agent. This mixing step is preferably performed at the time of use, just before applying to the hair the composition resulting from the mixing.

According to this embodiment, the process for dyeing keratin fibres, preferably the hair, according to the invention, comprises the step of applying to the keratin fibres a composition resulting from the mixing, at the time of use, of at least two compositions:

a) a dye composition comprising:

one or more oxidation dyes chosen from at least one coupler chosen from: 6-hydroxybenzomorpholine of formula (I), the addition salts thereof, the solvates thereof and/or the solvates of the salts thereof, hyd-oxyethyl-3,4-methylenedioxyaniline of formula (II), the addition salts thereof, the solvates thereof and/or the solvates of the salts thereof, 2-amino-5-ethylphenol of formula (III), the addition salts thereof, the solvates thereof and/or the solvates of the salts thereof, and mixtures thereof;

(I)

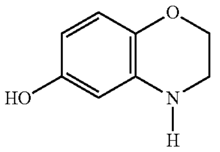

(II)

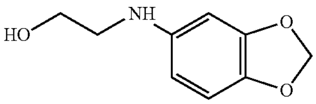

(III)

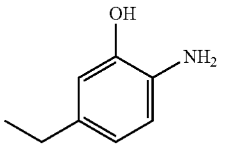

and at least one base chosen from: 2-p-hydroxyethyl-para-phenylenediamine and the addition salts thereof, the solvates thereof and/or the solvates of salts thereof, 2-(γ-hydroxypropyl)-para-phenylenediamine and the addition salts thereof, the solvates thereof and/or the solvates of salts thereof, 2-methoxymethyl-para-phenylenediamine and the addition salts thereof, the solvates thereof and/or the solvates of salts thereof, and mixtures thereof;

1,3-propanediol;

at least one alkaline agent;

at least one fatty substance other than fatty acids, and b) an oxidizing composition comprising one or more chemical oxidizing agents, preferably hydrogen peroxide.

In a preferred embodiment, the process for dyeing keratin fibres, preferably the hair, according to the invention, comprises the step of applying to the keratin fibres a composition resulting from the mixing, at the time of use, of at least two compositions:

a) a dye composition comprising:

at least one coupler chosen from: 6-hydroxybenzomorpholine of formula (I), the addition salts thereof, the solvates thereof and/or the solvates of the salts thereof, hydroxyethyl-3,4-methylenedioxyaniline of formula (II), the addition salts thereof, the solvates thereof and/or the solvates of the salts thereof, 2-amino-5-ethylphenol of formula (III), the addition salts thereof, the solvates thereof and/or the solvates of the salts thereof, and mixtures thereof;

(I)

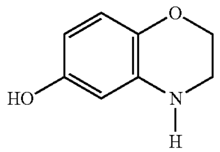

(II)

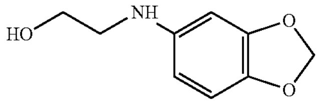

(III)

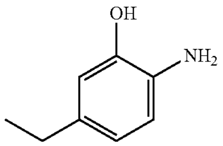

1,3-propanediol;

at least one alkaline agent;

at least one fatty substance other than fatty acids;

at least one surfactant;

at least one oxidation base; and b) an oxidizing composition comprising one or more chemical oxidizing agents, preferably hydrogen peroxide.

More particularly, the chemical oxidizing agent(s) are chosen from hydrogen peroxide, urea peroxide, alkali metal bromates or ferricyanides, peroxygenated salts, for instance persulfates, perborates, peracids and precursors thereof and percarbonates of alkali metals or alkaline-earth metals, and mixtures thereof. The oxidizing agent is preferably chosen from hydrogen peroxide.

The oxidizing composition is preferably an aqueous composition. In particular, it comprises more than 5% by weight of water, preferably more than 10% by weight ofwater and even more advantageously more than 20% by weight of water.

It may also comprise one or more organic solvents chosen from those listed previously; these solvents more particularly representing, when they are present, from 1% to 40% by weight and preferably from 5% to 30% by weight, relative to the weight of the oxidizing composition.

The oxidizing composition also preferably comprises one or more acidifying agents. Among the acidifying agents, examples that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

The oxidizing composition may also comprise fatty substances such as those described previously, preferably chosen from fatty alcohols, liquid hydrocarbons comprising more than 16 carbon atoms and mixtures thereof, surfactants and polymers.

Usually, the pH of the oxidizing composition, when it is aqueous, is less than 7.

Preferably, the oxidizing composition comprises hydrogen peroxide as oxidizing agent, in aqueous solution, the concentration of which ranges, more particularly, from 0.1% to 50%, more particularly between 0.5% and 20% and even more preferentially between 1% and 15% by weight, relative to the weight of the oxidizing composition.

Preferably, at least one of the compositions (dye composition or oxidizing composition) is aqueous.

Kit

Another subject of the invention is a multi-compartment device, preferably comprising two compartments, for dyeing keratin fibres, preferably the hair, comprising at least a first compartment containing the dye composition according to the invention and at least a second compartment containing an oxidizing composition as described above.

The compositions of the device according to the invention are packaged in separate compartments, optionally accompanied by suitable application means, which may be identical or different, such as fine brushes, coarse brushes or sponges.

The device mentioned above may also be equipped with a means for dispensing the desired mixture on the hair, for instance the devices described in patent FR 2 586 913.

Finally, the present invention relates to the use of a composition as described above, for dyeing keratin fibres, and in particular the hair.

The examples that follow serve to illustrate the invention without, however, being limiting in nature.

EXAMPLES

In the examples that follow, all the amounts are given as mass percentages of active material (AM) relative to the total weight of the composition (unless otherwise mentioned).

Example 1

Composition

The dye compositions A1 and A2 and the oxidizing composition O were prepared from the ingredients of which the contents are indicated in the table below (% AM):

Dye Compositions

TABLE 1

| | A1 (invention) | A2 (comparative) |
|---|---|---|
| Xanthan gum | 0.2 | 0.2 |
| Oleic acid | 2.7 | 2.7 |
| Ethanolamine | 12.2 | 12.2 |
| Coco glucoside | 1.87 | 1.87 |
| Hydroxybenzomorpholine | 0.3 | 0.3 |
| 2-Methoxymethyl-p-phenylenediamine | 0.3 | 0.3 |
| 1,3-Propanediol | 5 | — |
| Propylene glycol | — | 5 |
| Tetrasodium glutamate diacetate | 0.24 | 0.24 |
| Glycerol | 5 | 5 |
| Cetearyl alcohol | 16.3 | 16.3 |
| Oleyl alcohol | 2.7 | 2.70 |
| Water | qs 100 | qs 100 |

Oxidizing Composition

TABLE 2

| | O |
|---|---|
| Trideceth-2 carboxamide MEA | 0.85 |
| Tetrasodium etidronate | 0.06 |
| Sodium salicylate | 0.035 |
| Glycerol | 0.5 |
| Cetearyl alcohol | 2.28 |
| Ceteareth-25 | 0.57 |
| Phosphoric acid | qs pH = 2.2 ± 0.2 |
| Hydrogen peroxide | 6 |
| Tetrasodium pyrophosphate | 0.04 |
| Water | qs 100 |

At the time of use, each of the dye compositions A1 and A2 is mixed with 1.5 times its weight of oxidizing agent O. Each of the mixtures is then applied to locks of moderately sensitized hair (alkaline solubility 20%), in a proportion of 5 g of mixture/g of hair.

After a leave-on time of 30 minutes on a plate thermostatically regulated at 27° C., the hair is rinsed, washed with a standard shampoo and dried.

Results

The colorimetric measurements were performed using a Konica Minolta 3600 spectrocolorimeter (illuminant D65, angle 10°, specular component included) in the CIELab system.

In this system, L* represents the luminance.

The lower the L* value, the more powerful the colouring obtained.

TABLE 3

| | L* |
|---|---|
| A1 + O (invention) | 36.6 |
| A2 + O (comparative) | 40.0 |

The composition A1 according to the invention comprising 1,3-propanediol leads to a better colouring power, in comparison with the comparative composition A2 comprising propylene glycol.

Example 2

Compositions

The dye composition A3 was prepared from the ingredients of which the contents are indicated in the table below (% AM):

Dye Composition

TABLE 4

| | A3 |
|---|---|
| XANTHAN GUM | 0.2 |
| OLEIC ACID | 2.7 |
| ETHANOLAMINE | 12.7 |
| COCO-GLUCOSIDE | 1.87 |
| HYDROXYETHYL-3,4-METHYLENEDIOXYANILINE HCL | 0.3 |
| HYDROXYPROPYL-P-PHENYLENEDIAMINE HCL | 0.3 |
| 1,3-PROPANEDIOL | 5 |
| TETRASODIUM GLUTAMATE DIACETATE | 0.24 |
| GLYCERIN | 5 |

TABLE 4-continued

| | A3 |
|---|---|
| CETEARYL ALCOHOL | 16.3 |
| OLEYL ALCOHOL | 2.7 |
| WATER | Qs 100 |

At the time of use, composition A3 is mixed with 1.5 times its weight of oxidizing agent O disclosed in example 1.

The mixtures is then applied to locks of 90% permanent-waved grey hair, in a proportion of 5 g of mixture/g of hair.

After a leave-on time of 30 minutes on a plate thermostatically regulated at 27° C., the hair is rinsed, washed with a standard shampoo and dried.

Results

The colorimetric measurements were performed using a Konica Minolta CM-3600A spectrocolorimeter (illuminant D65, angle 10°, specular component included) in the CIELab system.

The chromaticity is calculated by the following formula:

$$C^* = \sqrt{(a^*)^2 + (b^*)^2}$$

a* indicates the green/red color axis b* indicates the blue/yellow color axis

The higher the value of the chromaticity C*, the greater the chromaticity is.

The composition according to the invention leads to a high C* value, and thus to a good chromaticity.

The invention claimed is:

1. A composition comprising:

at least one oxidation dye chosen from:

(i) at least one coupler chosen from: 6-hydroxybenzomorpholine of formula (I), addition salts thereof, solvates thereof and/or the solvates of salts thereof; hydroxyethyl-3,4-methylenedioxyaniline of formula (II), addition salts thereof, solvates thereof and/or the solvates of salts thereof; or 2-amino-5-ethylphenol of formula (III), addition salts thereof, solvates thereof and/or the solvates of salts thereof;

(I)

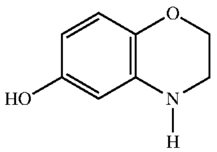

(II)

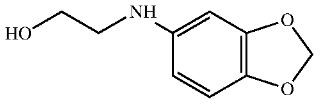

(III)

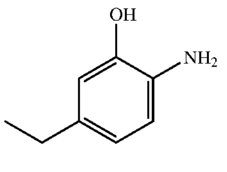

(ii) at least one base chosen from: 2-β-hydroxyethyl-para-phenylenediamine and addition salts thereof, solvates thereof and/or the solvates of salts thereof; 2-(γ-hydroxypropyl)-para-phenylenediamine and addition salts thereof, solvates thereof and/or the solvates of salts thereof; or 2-methoxymethyl-para-phenylenediamine and addition salts thereof, solvates thereof and/or the solvates of salts thereof; or (iii) mixtures of any two or more oxidation dyes thereof;

propane-1,3-diol;

at least one alkaline agent; and at least one fatty substance other than fatty acids.

2. The composition of claim 1, wherein the at least one oxidation dye is chosen from the (i) coupler(s).

3. The composition of claim 2, wherein the total amount of the coupler(s) (i) ranges from 0.001% to 20% by weight, relative to the total weight of the composition.

4. The composition of claim 1, wherein the total amount of propane-1,3-diol ranges from 0.01% to 25% by weight, relative to the total weight of the composition.

5. The composition of claim 1, wherein the at least one alkaline agent is chosen from alkanolamines.

6. The composition of claim 1, wherein the total amount of the alkaline agent(s) ranges from 0.1% to 40% by weight, relative to the total weight of the composition.

7. The composition of claim 1, wherein the at least one fatty substance other than fatty acids comprises at least one liquid fatty substance other than fatty acids.

8. The composition of claim 1, wherein the at least one fatty substance other than fatty acids comprises at least one solid fatty substance other than fatty acids.

9. The composition of claim 1, wherein the total amount of fatty substance(s) other than fatty acids ranges from 5% to 30% by weight, relative to the total weight of the composition.

10. The composition of claim 8, wherein the total amount of solid fatty substance(s) other than fatty acids ranges from 5% to 30% by weight, relative to the total weight of the composition.

11. The composition of claim 7, wherein the total amount of liquid fatty substance(s) other than fatty acids ranges from 0.5% to 15% by weight, relative to the total weight of the composition.

12. The composition of claim 1, further comprising (iii) at least one additional coupler other than the (ii) at least one coupler.

13. The composition of claim 1, further comprising at least one surfactant.

14. The composition of claim 13, wherein the at least one surfactant is chosen from anionic surfactants, nonionic surfactants, or mixtures thereof.

15. The composition of claim 1, further comprising at least one sequestrant.

16. The composition of claim 1, further comprising at least one thickening polymer.

17. The composition of claim 1, wherein the composition is free of any chemical oxidizing agents.

18. The composition of claim 1, further comprising at least one chemical oxidizing agent.

19. A method for dyeing keratin fibres, comprising mixing at least a dyeing composition and an oxidizing composition, wherein the dyeing composition comprises:

at least one coupler chosen from: 6-hydroxybenzomorpholine of formula (I), addition salts thereof, solvates thereof and/or the solvates of salts thereof; hydroxyethyl-3,4-methylenedioxyaniline of formula (II), addition salts thereof, solvates thereof and/or the solvates of salts thereof; 2-amino-5-ethylphenol of formula (III), addition salts thereof, solvates thereof and/or the solvates of salts thereof; or mixtures thereof;

(I)

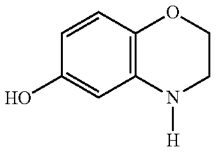

(II)

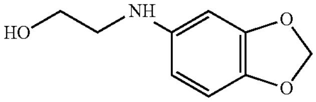

(III)

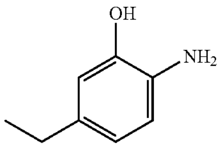

propane-1,3-diol;

at least one alkaline agent;

at least one fatty substance other than fatty acids; and optionally at least one oxidation base; and wherein the oxidizing composition comprises at least one chemical oxidizing agent.

20. A multi-compartment device, comprising:

at least a first compartment comprising a dyeing composition comprising:

at least one coupler chosen from: 6-hydroxybenzomorpholine of formula (I), addition salts thereof, solvates thereof and/or the solvates of salts thereof; hydroxyethyl-3,4-methylenedioxyaniline of formula (II), addition salts thereof, solvates thereof and/or the solvates of salts thereof; 2-amino-5-ethylphenol of formula (III), addition salts thereof, solvates thereof and/or the solvates of salts thereof; or mixtures thereof;

(I)

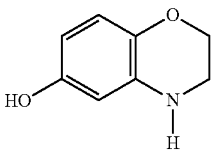

(II)

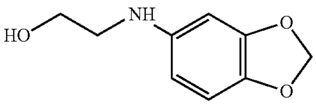

(III)

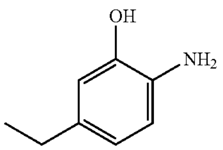

propane-1,3-diol;

at least one alkaline agent;

at least one fatty substance other than fatty acids; and optionally at least one oxidation base; and at least a second compartment comprising an oxidizing composition comprising at least one chemical oxidizing agent.

* * * * *